US012575734B2

(12) United States Patent

Schmidt et al.

(10) Patent No.: US 12,575,734 B2

(45) Date of Patent: Mar. 17, 2026

(54) DEVICES AND RELATED ASPECTS FOR MAGNETIC RESONANCE IMAGING-BASED IN-SITU TISSUE CHARACTERIZATION

(71) Applicant: THE JOHNS HOPKINS UNIVERSITY, Baltimore, MD (US)

(72) Inventors: Ehud J. Schmidt, Towson, MD (US); Yue Chen, Boston, MA (US); Akila Viswanathan, Baltimore, MD (US); Henry R. Halperin, Baltimore, MD (US); Junichi Tokuda, Boston, MA (US); Anthony Gunderman, Fayetteville, AR (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 412 days.

(21) Appl. No.: 17/793,144

(22) PCT Filed: Jan. 14, 2021

(86) PCT No.: PCT/US2021/013493

§ 371 (c)(1),
(2) Date: Jul. 15, 2022

(87) PCT Pub. No.: WO2021/146465

PCT Pub. Date: Jul. 22, 2021

(65) Prior Publication Data

US 2023/0065974 A1 Mar. 2, 2023

Related U.S. Application Data

(60) Provisional application No. 63/035,606, filed on Jun. 5, 2020, provisional application No. 63/019,868, filed (Continued)

(51) Int. Cl.
A61B 5/00 (2006.01)
A61B 5/055 (2006.01)

(Continued)

(52) U.S. Cl.
CPC ............ A61B 5/0036 (2018.08); A61B 5/055 (2013.01); A61B 34/20 (2016.02); G01R 33/287 (2013.01);

(Continued)

(58) Field of Classification Search
CPC ................ A61N 5/1007; A61N 5/1027; A61N 2005/1012; A61N 5/1001;

(Continued)

(56) References Cited

U.S. PATENT DOCUMENTS

2001/0056232 A1* 12/2001 Lardo ...................... H01Q 1/40
600/423
2003/0187347 A1* 10/2003 Nevo ..................... A61B 5/415
600/424

(Continued)

FOREIGN PATENT DOCUMENTS

WO 2010022278 2/2010
WO WO-2018071591 A1 * 4/2018 ........... A61B 5/6851

OTHER PUBLICATIONS

Downey, K., Attygalle, A. D., Morgan, V. A., Giles, S. L., MacDonald, A., Davis, M., . . . & deSouza, N. M. (2016). Comparison of optimised endovaginal vs external array coil T2-weighted and diffusion-weighted imaging techniques . . . European radiology, 26, 941-950. (Year: 2016).*

(Continued)

*Primary Examiner* — Keith M Raymond
*Assistant Examiner* — Johnathan Maynard
(74) *Attorney, Agent, or Firm* — MH2 Technology Law Group LLP

(57) ABSTRACT

Provided herein are methods of analyzing tissue using a magnetic resonance imaging (MRI) compatible tissue analysis device that includes radio-frequency (RF) tracking and (Continued)

500

501 503 505 507 imaging elements. Related kits, systems, and computer program products are also provided.

19 Claims, 28 Drawing Sheets

Related U.S. Application Data on May 4, 2020, provisional application No. 62/961,490, filed on Jan. 15, 2020.

(51) Int. Cl.

| | |
|---|---|
| *A61B 5/06* | (2006.01) |
| *A61B 17/00* | (2006.01) |
| *A61B 17/34* | (2006.01) |
| *A61B 34/20* | (2016.01) |
| *A61B 90/00* | (2016.01) |
| *A61N 5/10* | (2006.01) |
| *G01R 33/28* | (2006.01) |
| *G01R 33/34* | (2006.01) |

(52) U.S. Cl.
CPC .............. *G01R 33/34* (2013.01); *A61B 5/062* (2013.01); *A61B 2017/00323* (2013.01); *A61B 2017/00911* (2013.01); *A61B 2017/3411* (2013.01); *A61B 2034/2051* (2016.02); *A61B 2090/374* (2016.02); *A61B 2090/3958* (2016.02); *A61N 5/1001* (2013.01); *A61N 5/1007* (2013.01); *A61N 2005/1012* (2013.01); *A61N 5/1027* (2013.01)

(58) Field of Classification Search
CPC . A61B 2017/3411; A61B 34/20; A61B 5/055; A61B 2034/2051; A61B 33/287; A61B 2017/00911; A61B 2090/374; A61B 17/3403; A61B 2090/3954; A61B 5/062; A61B 34/10; A61B 1/00154; A61B 17/3468; A61B 18/1492; A61B 2034/107; A61B 5/06; A61B 5/065; A61B 90/11; G01R 33/287; G01R 33/34084; G01R 33/285; G01R 33/34007; G01R 33/286; G01R 33/34053; G01R 33/341; G01R 33/3621; G01R 33/5608; G01R 33/56563; A61M 2025/0166; A61M 2025/0681; A61M 2025/09175; A61M 25/01
See application file for complete search history.

(56) References Cited

U.S. PATENT DOCUMENTS

| | | | | |
|---|---|---|---|---|
| 2006/0122493 | A1* | 6/2006 | Atalar | ................. A61B 5/4381 |
| | | | | 600/423 |
| 2007/0112342 | A1 | 5/2007 | Pearson et al. | |
| 2009/0118729 | A1 | 5/2009 | Auth et al. | |
| 2011/0134113 | A1 | 6/2011 | Ma et al. | |
| 2013/0123598 | A1* | 5/2013 | Jenkins | ................. A61B 5/283 |
| | | | | 600/374 |
| 2015/0338477 | A1* | 11/2015 | Schmidt | ................ A61B 5/062 |
| | | | | 600/417 |
| 2017/0007148 | A1* | 1/2017 | Kaditz | ................... A61B 5/055 |
| 2017/0135723 | A1* | 5/2017 | Zarembinski | ...... A61B 17/3423 |
| 2018/0116519 | A1 | 5/2018 | Piron et al. | |
| 2020/0037917 | A1* | 2/2020 | Schmidt | ............. G01R 33/3621 |
| 2022/0401124 | A1* | 12/2022 | Sánchez López | ..... A61B 34/10 |

OTHER PUBLICATIONS

Alipour, A., Meyer, E., Elahi, H., Fink, S., Halperin, H., Viswanathan, A., & EJ, S. (2019). Cervical-Cancer Imaging for brachytherapy planning employing an endo-vaginal array that includes an enhanced forward-looking coil. In Proceedings ISMRM. (Year: 2019).*

Fields, E. C., Hazell, S., Morcos, M., Schmidt, E. J., Chargari, C., & Viswanathan, A. N. (2019). Image-guided gynecologic brachytherapy for cervical cancer. In Seminars in radiation oncology (vol. 30, No. 1, pp. 16-28). WB Saunders. (Year: 2019).*

De Arcos, J., Schmidt, E. J., Wang, W., Tokuda, J., Vij, K., Seethamraju, R. T., . . . & Viswanathan, A. N. (2017). Prospective clinical implementation of a novel magnetic resonance tracking device . . . International Journal of Radiation Oncology* Biology* Physics, 99(3), 618-626. (Year: 2017).*

Chen, Y., Wang, W., Schmidt, E. J., Kwok, K. W., Viswanathan, A. N., Cormack, R., & Tse, Z. T. H. (2015). Design and fabrication of MR-tracked metallic stylet for gynecologic brachytherapy. IEEE/ASME Transactions on Mechatronics, 21(2), 956-962. (Year: 2015).*

Wang, W., Viswanathan, A. N., Damato, A. L., Chen, Y., Tse, Z., Pan, L., . . . & Cormack, R. A. (2015). Evaluation of an active magnetic resonance tracking system for interstitial brachytherapy. Medical physics, 42(12), 7114-7121. (Year: 2015).*

Wang, W., Dumoulin, C. L., Viswanathan, A. N., Tse, Z. T., Mehrtash, A., Loew, W., . . . & Schmidt, E. J. (2015). Real-time active MR-tracking of metallic stylets in MR-guided radiation therapy. Magnetic resonance in medicine, 73(5), 1803-1811. (Year: 2015).*

Alipour, A., Meyer, E. S., Dumoulin, C. L., Watkins, R. D., Elahi, H., Loew, W., . . . & Schmidt, E. J. (2019). MRI conditional actively tracked metallic electrophysiology catheters and guidewires with miniature tethered radio-frequency traps. IEEE Transactions on Biomedical Engineering, 67(6), 1616-1627 (Year: 2019).*

Yak, N., Anderson, K. J., & Wright, G. A. (2012). Tuning and amplification strategies for intravascular imaging coils. Magnetic Resonance in Medicine, 68(5), 1675-1680. (Year: 2012).*

International Search Report and Written Opinion in corresponding International Application No. PCT/US2021/013493 mailed on Apr. 14, 2021, 9 pages.

Gunderman, Anthony L. et al. "MR-Guided Tissue Puncture with On-Line Imaging for High-Resolution Theranostics," 2020 International Symposium on Medical Robotics (ISMR), Atlanta, GA, USA, 2020, pp. 57-61, doi: 10.1109/ISMR48331.2020.9312942.

* cited by examiner

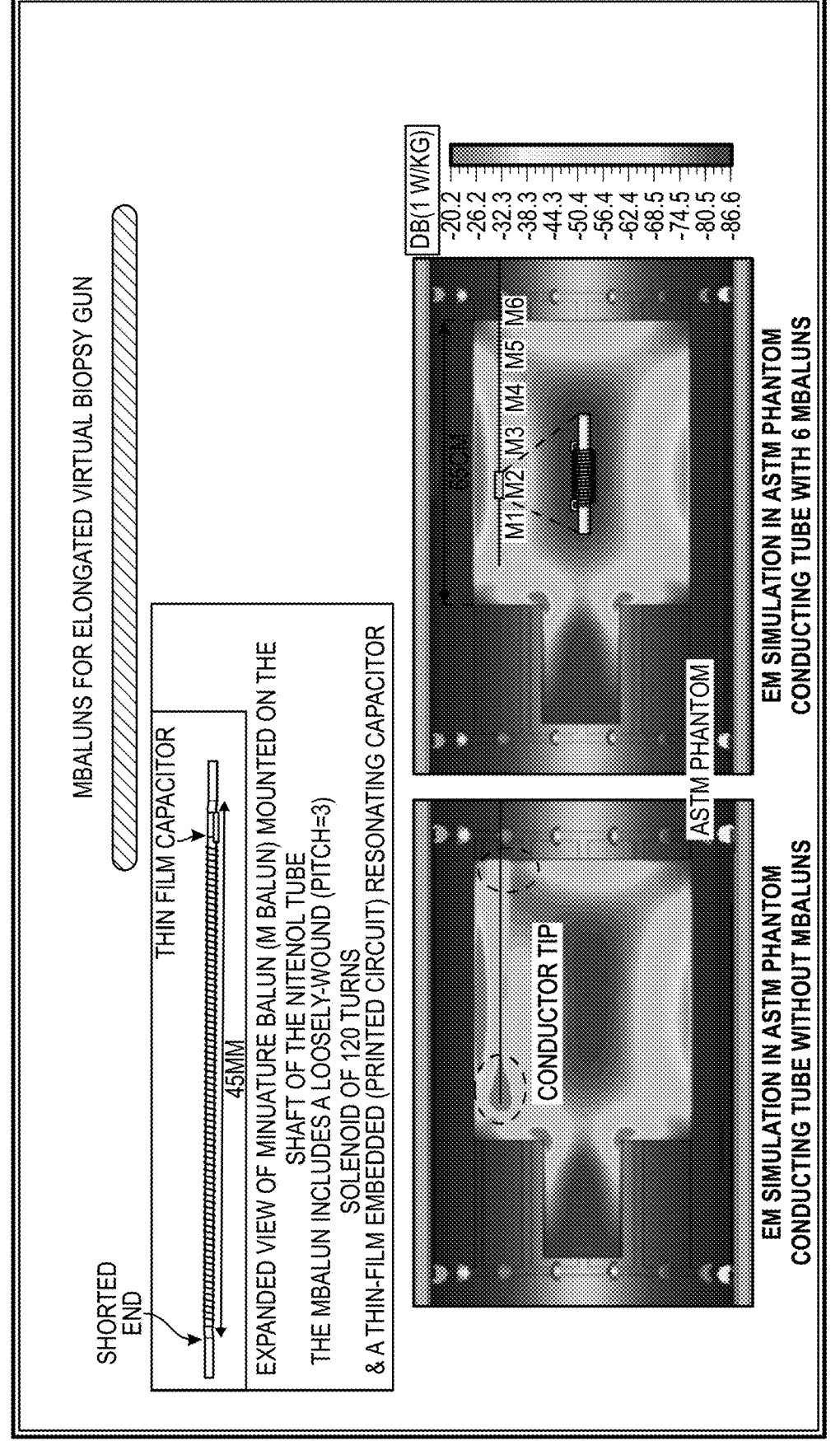

MBALUNS FOR ELONGATED VIRTUAL BIOPSY GUN

THIN FILM CAPACITOR

45MM

SHORTED END

EXPANDED VIEW OF MINIATURE BALUN (M BALUN) MOUNTED ON THE SHAFT OF THE NITENOL TUBE
THE MBALUN INCLUDES A LOOSELY-WOUND (PITCH=3) SOLENOID OF 120 TURNS
& A THIN-FILM EMBEDDED (PRINTED CIRCUIT) RESONATING CAPACITOR

DB(1 W/KG)
-20.2
-26.2
-32.3
-38.3
-44.3
-50.4
-56.4
-62.4
-68.5
-74.5
-80.5
-86.6

M1 M2 M3 M4 M5 M6

ASTM PHANTOM

CONDUCTOR TIP

EM SIMULATION IN ASTM PHANTOM CONDUCTING TUBE WITHOUT MBALUNS

EM SIMULATION IN ASTM PHANTOM CONDUCTING TUBE WITH 6 MBALUNS

FIG. 1

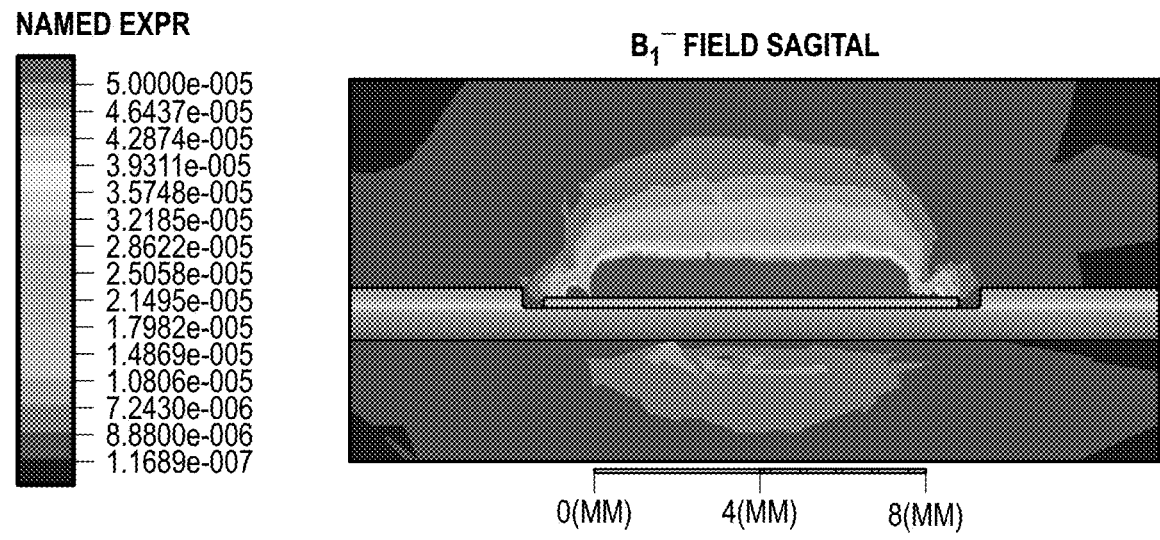

NAMED EXPR

5.0000e-005
4.6437e-005
4.2874e-005
3.9311e-005
3.5748e-005
3.2185e-005
2.8622e-005
2.5058e-005
2.1495e-005
1.7982e-005
1.4869e-005
1.0806e-005
7.2430e-006
8.8800e-006
1.1689e-007

$B_1^-$ FIELD SAGITAL

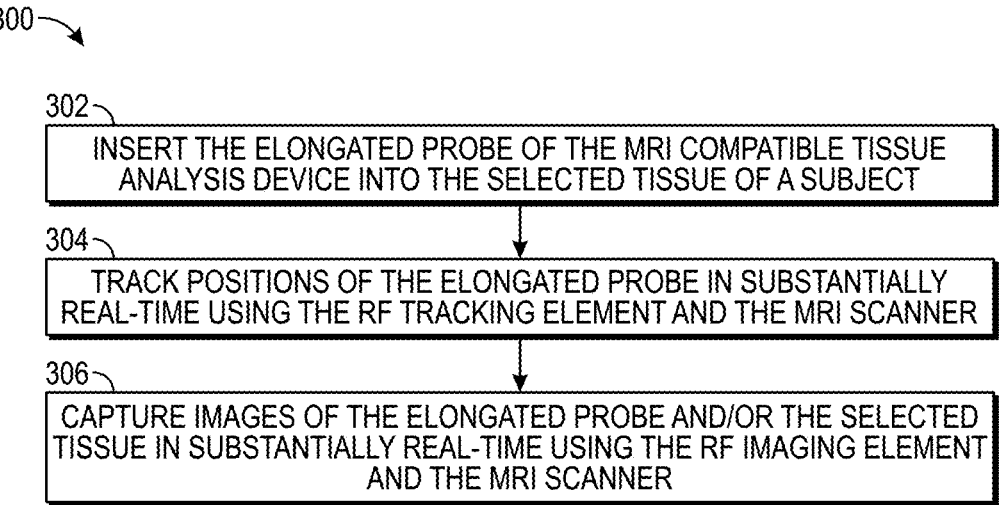

300

302 — INSERT THE ELONGATED PROBE OF THE MRI COMPATIBLE TISSUE ANALYSIS DEVICE INTO THE SELECTED TISSUE OF A SUBJECT

304 — TRACK POSITIONS OF THE ELONGATED PROBE IN SUBSTANTIALLY REAL-TIME USING THE RF TRACKING ELEMENT AND THE MRI SCANNER

306 — CAPTURE IMAGES OF THE ELONGATED PROBE AND/OR THE SELECTED TISSUE IN SUBSTANTIALLY REAL-TIME USING THE RF IMAGING ELEMENT AND THE MRI SCANNER

FIG. 3

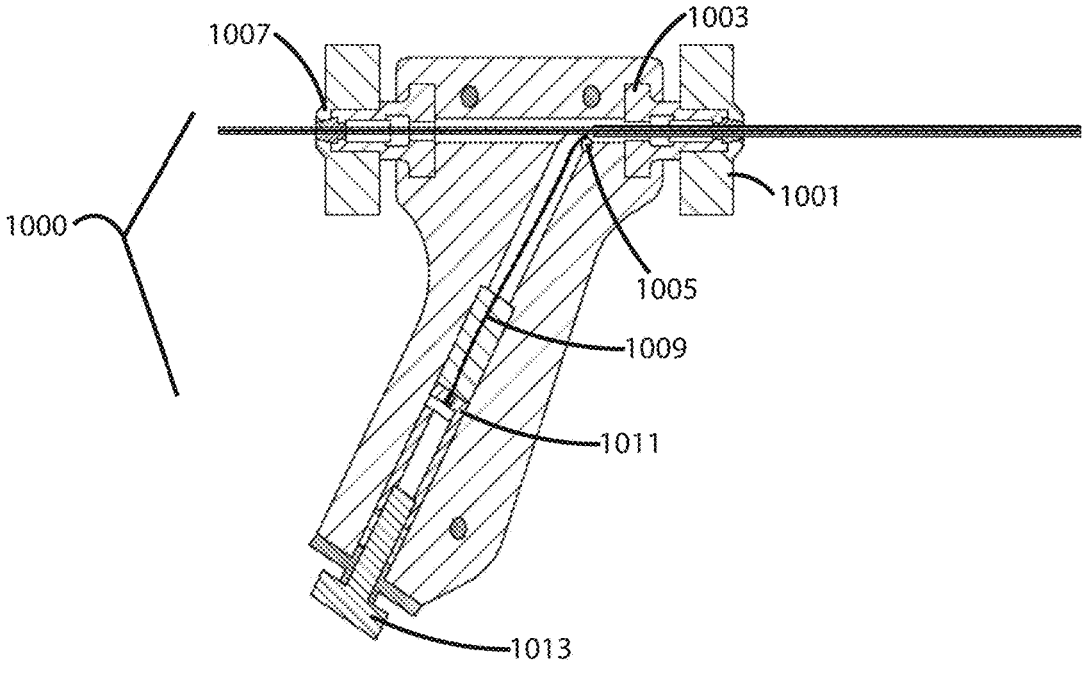
FIG. 10
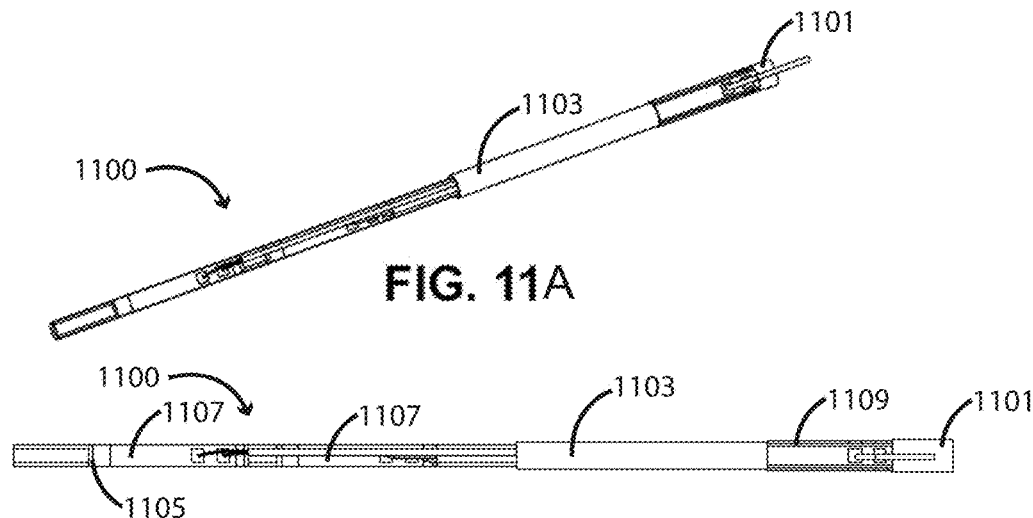
FIG. 11A
FIG. 11B

1200

1201

1203

1205

1207    1209    1211

1200

1211

1201

1207

1213    1215

PROFILE

DEVICES AND RELATED ASPECTS FOR MAGNETIC RESONANCE IMAGING-BASED IN-SITU TISSUE CHARACTERIZATION

CROSS-REFERENCE TO RELATED APPLICATIONS

The present application is the national stage entry of International Patent Application No. PCT/US2021/013493, filed on Jan. 14, 2021, and published as WO 2021/146465 A1 on Jul. 22, 2021, which claims the benefit of U.S. Provisional Patent Application Ser. Nos. 62/961,490, filed Jan. 15, 2020, 63/019,868, filed May 4, 2020, and 63/035, 606, filed Jun. 5, 2020, the entire disclosures of which are incorporated herein by reference.

STATEMENT REGARDING FEDERALLY SPONSORED RESEARCH OR DEVELOPMENT

This invention was made with government support under R01HL094610 and R01EB020667 awarded by the National Institutes of Health. The government has certain rights in the invention.

BACKGROUND

During treatments that involve radiation or ablation, it is paramount to characterize tissue properties, such as evaluating the response of the tissue to their respective treatment [Kabalin et al., "Identification of residual cancer in the prostate following radiation therapy: role of transrectal ultrasound guided biopsy and prostate specific antigen," The Journal of Urology, 142:326-331 (1989), Taskin et al., "Long-term histopathologic and morphologic changes after thermal endometrial ablation," The Journal of the American Association of Gynecologic Laparoscopists, 9:186-190 (2002)]. Evaluating tissue properties is traditionally performed by removal of the tissue, followed by the pathological characterization. Alternatively, tissue biopsy can be accomplished in-situ, using tools such as Optical Coherence Tomography (OCT) [Huang et al., "Optical coherence tomography," Science, 254:1178-1181 (1991)] and Intravascular Ultrasound (IVUS) [Nishimura et al., "Intravascular ultrasound imaging: in vitro validation and pathologic correlation," Journal of the American College of Cardiology, 16:145-154 (1990)]. The advantages of these tools include (i) the ability to perform scans that span extended distances, rather than sample only at discrete locations, (ii) perform the analyses quickly, in order to provide rapid reports and visualize dynamic process, and (iii) their minimally invasive nature. However, there are limitations to OCT and IVUS, particularly with respect to tissue visualization depth; IVUS penetrates 4-7 mm inside the vessel wall, while OCT penetrates 2-3 mm, limiting both visualization techniques to structures reachable by the vascular system [Maehara et al., "Advances in intravascular imaging," Circulation: Cardiovascular Interventions, 2:482-490 (2009)].

Accordingly, there is a need for additional methods, and related aspects, for high-resolution in-situ tissue theranostics with enhanced visualization depths.

SUMMARY

The present disclosure relates, in certain aspects, to methods, devices, kits, systems, and computer readable media of use in analyzing tissue disposed in-situ in subjects or otherwise disposed (e.g., ex-vivo, in-vitro, etc.). In certain applications, for example, the devices and related aspects are used to image tissue within a subject to detect the presence of cancerous cells or other disease states within the imaged tissues in substantially real-time. In some of these applications, the devices are also configured to convey therapeutic agents to that tissue to treat the detected disease. These and other aspects will be apparent upon a complete review of the present disclosure, including the accompanying figures.

In certain aspects, the devices disclosed herein are intended to provide a virtual biopsy in tissues utilizing holes that are created in the tissue of a given subject for diagnostic and/or therapeutic purposes. Examples for such therapeutic purposes include interstitial radiation therapy (brachytherapy), percutaneous ablation therapy, among many others. To further illustrate, the devices disclosed herein can be used as an aid in performing theranostics, namely the trial of a variety of methods to detect and treat a given medical condition. Examples include the trial of chemical and biologic substances to treat a cancer, the trial of agents to reduce acute and chronic pain, and the trial of agents to test response of tissue to genetically targeted agents, and the like. Exemplary advantages of certain embodiments the devices disclosed herein include that (i) the time for imaging to be performed is typically reduced relative to conventional approaches, thereby providing a rapid report of the acquired data to users, (ii) the time for administered therapeutic agents to enter the targeted tissue (e.g., via diffusion or perfusion) is short, and (iii) the therapy is highly localized, so that reduced doses of a given therapeutic agent are typically needed, which thereby reduces side effects associated with those agents.

In one aspect, the present disclosure provides a magnetic resonance imaging (MRI) compatible tissue analysis device. The device includes at least one elongated probe insertable into at least one tissue, at least one radio-frequency (RF) tracking element operably connected to the elongated probe, which RF tracking element is operably connected, or connectable, to at least one MRI apparatus that is configured to track positioning of the elongated probe in substantially real-time at least when the elongated probe is inserted into the tissue, and at least one RF imaging element operably connected to the elongated probe, which RF imaging element is operably connected, or connectable, to the MRI apparatus that is further configured to capture one or more images of the elongated probe and/or the tissue in substantially real-time at least when the elongated probe is inserted into the tissue. In addition, the device also includes at least one deflection mechanism operably connected at least to the elongated probe, which deflection mechanism is configured to selectively deflect positioning of at least a portion of the elongated probe and at least one handle operably connected at least to the elongated probe.

In another aspect, the present disclosure provides a magnetic resonance imaging (MRI) compatible tissue analysis device. The device comprises at least one sheath comprising at least one channel disposed at least partially therethrough, at least one elongated probe at least partially disposed and selectively movable within the channel of the sheath, which elongated probe is insertable into at least one tissue, and at least one radio-frequency (RF) tracking element operably connected to the elongated probe, which RF tracking element is operably connected, or connectable, to at least one MRI apparatus that is configured to track positioning of the elongated probe in substantially real-time at least when the elongated probe is inserted into the tissue. The device also includes at least one RF imaging element operably connected to the elongated probe and/or the sheath, which RF imaging element is operably connected, or connectable, to the MRI apparatus that is further configured to capture one or more images of the elongated probe and/or the surrounding tissue in substantially real-time at least when the elongated probe is inserted into the tissue. In addition, the device also includes at least one deflection mechanism operably connected at least to the elongated probe, which deflection mechanism is configured to selectively deflect positioning of at least a portion of the elongated probe, and at least one handle operably connected at least to the sheath.

In another aspect, the present disclosure provides a magnetic resonance imaging (MRI) compatible tissue analysis device that includes at least one elongated probe insertable into at least one tissue, which elongated probe comprises at least one cavity and at least one deflectable region. The device also includes at least one radio-frequency (RF) tracking element operably connected to the elongated probe. The RF tracking element is operably connected, or connectable, to at least one MRI apparatus via at least one co-axial cable that is at least partially disposed within the cavity. The MRI apparatus is configured to track positioning of the elongated probe in substantially real-time at least when the elongated probe is inserted into the tissue. The device also includes at least one RF imaging element operably connected to the elongated probe. The RF imaging element is operably connected, or connectable, to the MRI apparatus via the co-axial cable that is at least partially disposed within the cavity. The MRI apparatus is further configured to capture one or more images of the elongated probe and/or the tissue in substantially real-time at least when the elongated probe is inserted into the tissue. The device also includes at least one handle operably connected at least to the elongated probe. In addition, the device also includes at least one deflection mechanism operably connected at least to the elongated probe. The deflection mechanism comprises at least one tendon operably connected at least proximal to an end of the elongated probe that is insertable into the tissue and to a tension adjustment element operably connected to the handle, which tendon is at least partially disposed within the cavity and which tension adjustment element is configured to selectively effect deflection of positioning of at least a portion of the elongated probe, which portion of the elongated probe comprises the deflectable region.

In another aspect, the present disclosure provides a magnetic resonance imaging (MRI) compatible tissue analysis device that includes at least one elongated probe insertable into at least one tissue, and at least a portion of at least one axial rotational control mechanism operably connected, or connectable, to the elongated probe. The device also includes at least one radio-frequency (RF) tracking element operably connected to the elongated probe. The RF tracking element is operably connected, or connectable, to at least one MRI apparatus that is configured to track positioning of the elongated probe in substantially real-time at least when the elongated probe is inserted into the tissue. The device also includes at least one RF imaging element operably connected to the elongated probe. The RF imaging element is operably connected, or connectable, to the MRI apparatus that is further configured to capture one or more images of the elongated probe and/or the tissue in substantially real-time at least when the elongated probe is inserted into the tissue. In addition, the device also includes at least one deflection mechanism operably connected at least to the elongated probe, which deflection mechanism is configured to selectively deflect positioning of at least a portion of the elongated probe, and at least one handle operably connected at least to the elongated probe.

In certain embodiments, the elongated probe is fabricated from at least one flexible material. In some embodiments, the sheath and/or the elongated probe comprises at least one stylet. In certain embodiments, the elongated probe comprises at least one groove, wherein the RF tracking element and/or the RF imaging element is at least partially disposed within the groove. In some embodiments, the elongated probe comprises at least one cavity, wherein at least one co-axial cable is at least partially disposed within the cavity and operably connected to the RF tracking element and/or the RF imaging element and operably connected, or connectable, to the MRI apparatus. In some of these embodiments, the deflection mechanism comprises at least one tendon operably connected at least proximal to an end of the elongated probe that is insertable into the tissue and to a tension adjustment element operably connected to the handle, which tendon is at least partially disposed within the cavity and which tension adjustment element is configured to selectively effect deflection of the positioning of the portion of the elongated probe. In certain of these embodiments, the cavity is disposed substantially through a length of the elongated probe. In some of these embodiments, the elongated probe comprises at least one stylet. In certain of these embodiments, wherein the elongated probe comprises a deflectable tube that comprises the cavity. In some embodiments, the elongated probe comprises at least one deflectable region that deflects when the deflection mechanism selectively deflects positioning of the portion of the elongated probe. In certain of these embodiments, the deflectable region comprises at least one orifice disposed at least partially through the elongated probe. In certain of these embodiments, the orifice comprises at least one indentation disposed substantially perpendicular to a longitudinal axis of the elongated probe. In some of these embodiments, the orifice communicates with the cavity. In certain of these embodiments, the deflectable region comprises multiple orifices (e.g., an array of orifices, etc.) disposed at least partially through the elongated probe.

In certain embodiments, the device includes at least a portion of at least one axial rotational control mechanism operably connected, or connectable, to the device. In some of these embodiments, the axial rotational control mechanism comprises at least one dial indicator operably connected to the elongated probe, which dial indicator indicates at least one rotational angle formed between at least a portion of the elongated probe and at least one template device (e.g., brachytherapy template device or the like) when the elongated probe is inserted into the tissue. In certain embodiments, at least one dial is operably connected, or connectable, to the template device, which dial shows the rotational angle formed between the portion of the elongated probe and the template device when the elongated probe is inserted into the tissue.

In some embodiments, the device includes at least two RF tracking elements operably connected to the elongated probe, which RF tracking elements are each operably connected, or connectable, to the MRI apparatus. In certain embodiments, the RF tracking element comprises one or more micro-coils. In certain embodiments, the RF tracking element and the RF imaging element are operably connected to the MRI apparatus. In some embodiments, the RF tracking element comprises at least one antenna tuned, or tunable, to a magnetic resonance (MR) operational (Larmor) frequency.

In certain embodiments, the RF imaging element comprises one or more micro-coils. In some embodiments, the RF imaging element comprises at least one antenna tuned, or tunable, to a magnetic resonance (MR) operational (Larmor) frequency. In some embodiments, the RF imaging element comprises at least one outward-looking imaging array configured to provide outward-looking imaging. In some embodiments, the outward-looking RF imaging element is enhanced by the use of a design wherein an imaging element is placed on top of the metallic surface with a thin insulator placed between the element and the metal, with the thickness and shape of the insulator are optimized to extend the RF radiation pattern in predetermined directions. In certain embodiments, the device includes at least one covering disposed around at least a portion of the sheath and/or the elongated probe.

In some embodiments, the MRI apparatus comprises at least one MRI scanner. In certain embodiments, the deflection mechanism is configured to selectively deflect positioning of at least a tip of the elongated probe. In certain embodiments, the device includes at least one collet adapter operably connected to the handle and at least one collect nut adjustably engaged with the collet adapter, which collet adapter and collet nut are configured to adjustably limit radial and/or axial displacement of the elongated probe and/or the sheath relative to the handle. In some embodiments, one or more components of the device comprise one or more of titanium, aluminum, brass, hydroxyapatite (HA), polymethylmethacrylate (PMMA), polyether ether ketone (PEEK), polyethylene, acrylonitrile butadiene styrene (ABS), or combinations thereof. In some embodiments, a kit comprises the device.

In certain embodiments, the sheath and/or the elongated probe comprises at least one MRI compatible metal. In certain of these embodiments, the metal comprises at least one shape memory and/or super-elastic alloy. In some of these embodiments, the shape memory and/or super-elastic alloy comprises an alloy of nickel and titanium.

In certain embodiments, at least a portion of the sheath comprises an outer-diameter of between about 1 mm and about 5 mm. In some of these embodiments, the portion of the sheath comprises an outer-diameter of about 2.2 mm.

In some embodiments, the sheath and/or the elongated probe comprises at least one conduit that comprises at least first and second openings, wherein the conduit is configured to convey one or more materials (e.g., gases, liquids, solids, tissue samples, and the like) through the first opening and through the second opening, when the first opening is in communication with one or more material reservoirs and when the second opening is positioned at a selected location within or proximal to the tissue. In certain of these embodiments, the conduit is disposed through at least a portion of the elongated probe. In some of these embodiments, the material reservoirs comprise one or more materials. In some of these embodiments, the materials comprise one or more therapeutic agents (e.g., chemotherapeutic agents, immunotherapeutic agents, radiation formulations, and the like).

In certain embodiments, at least a portion of the elongated probe comprises an outer-diameter of between about 0.1 mm and about 5 mm. In some of these embodiments, the portion of the elongated probe comprises an outer-diameter of about 1.5 mm. In some embodiments, the elongated probe comprises a length capable of extending from the sheath of between about 1.0 mm and about 1000 mm. In certain of these embodiments, the length of the elongated probe capable of extending from the sheath is 330 mm.

In some embodiments, the deflection mechanism comprises at least one tendon operably connected at least proximal to an end of the elongated probe that is insertable into the tissue and to a tension adjustment element operably connected to the handle, which tension adjustment element is configured to selectively effect deflection of the positioning of the portion of the elongated probe. In certain of these embodiments, the tendon is fabricated from an alloy of nickel and titanium. In certain of these embodiments, the tension adjustment element comprises a rotary actuated nut operably connected to the tendon and a rotary knob that adjustably engages the rotary actuated nut. In some of these embodiments, the device includes at least one tendon guide element operably connected to the handle, which tendon guide element limits the load on the sheath when tension applied to the tendon is increased.

In another aspect, the present disclosure provides a system that includes at least one magnetic resonance imaging (MRI) compatible tissue analysis device comprising at least one elongated probe insertable into at least one tissue, at least one radio-frequency (RF) tracking element operably connected to the elongated probe, at least one RF imaging element operably connected to the elongated probe, at least one deflection mechanism operably connected at least to the elongated probe, which deflection mechanism is configured to selectively deflect positioning of the elongated probe, and at least one handle operably connected at least to the elongated probe. The system also includes at least one MRI apparatus operably connected, or connectable, to the RF tracking element and to the RF imaging element, which MRI apparatus comprises at least one controller that comprises, or is capable of accessing, computer readable media comprising non-transitory computer-executable instructions which, when executed by at least one electronic processor perform at least: tracking one or more positions of the elongated probe in substantially real-time at least when the elongated probe is inserted into the tissue, and capturing one or more images of the elongated probe and/or the tissue in substantially real-time at least when the elongated probe is inserted into the tissue.

In another aspect, the present disclosure provides a system that includes at least one magnetic resonance imaging (MRI) compatible tissue analysis device. The tissue analysis device includes at least one sheath comprising at least one channel disposed at least partially therethrough, and at least one elongated probe at least partially disposed and selectively movable within the channel of the sheath, which elongated probe is insertable into at least one tissue. The tissue analysis device also includes at least one radio-frequency (RF) tracking element operably connected to the elongated probe, and at least one RF imaging element operably connected to the elongated probe and/or the sheath. In addition, the tissue analysis device also includes at least one deflection mechanism operably connected at least to the elongated probe, which deflection mechanism is configured to selectively deflect positioning of the elongated probe, and at least one handle operably connected at least to the sheath. The system also includes at least one MRI apparatus operably connected, or connectable, to the RF tracking element and to the RF imaging element, which MRI apparatus comprises at least one controller that comprises, or is capable of accessing, computer readable media comprising non-transitory computer-executable instructions which, when executed by at least one electronic processor perform at least: tracking one or more positions of the elongated probe in substantially real-time at least when the elongated probe is inserted into the tissue, and capturing one or more images of the elongated probe and/or the tissue in substantially real-time at least when the elongated probe is inserted into the tissue.

In another aspect, the present disclosure provides a system that includes at least one magnetic resonance imaging (MRI) compatible tissue analysis device. The MRI compatible tissue analysis device includes at least one elongated probe insertable into at least one tissue, at least one radio-frequency (RF) tracking element operably connected to the elongated probe, and at least one RF imaging element operably connected to the elongated probe. The MRI compatible tissue analysis device also includes at least one deflection mechanism operably connected at least to the elongated probe, which deflection mechanism is configured to selectively deflect positioning of the elongated probe. The MRI compatible tissue analysis device also includes at least one handle operably connected at least to the elongated probe. The system also includes at least one housing (e.g., a system box) that comprises at least one signal amplification mechanism operably connected, or connectable, to the RF tracking element and to the RF imaging element, which signal amplification mechanism is configured to amplify one or more signals received from the RF tracking element and/or from the RF imaging element. In addition, the system also includes at least one MRI apparatus operably connected, or connectable, at least to the signal amplification mechanism, which MRI apparatus comprises at least one controller that comprises, or is capable of accessing, computer readable media comprising non-transitory computer-executable instructions which, when executed by at least one electronic processor perform at least: tracking one or more positions of the elongated probe in substantially real-time at least when the elongated probe is inserted into the tissue, and capturing one or more images of the elongated probe and/or the tissue in substantially real-time at least when the elongated probe is inserted into the tissue.

In certain embodiments of the systems disclosed herein, the signal amplification mechanism comprises one or more operably connected low-noise amplifiers (LNAs). In some of these embodiments, the housing comprises one or more operably connected tuning, matching, decoupling, patient isolation, imaging channel, and/or tracking channel circuit elements. In certain of these embodiments, the signal amplification mechanism is configured to measure the signals before and after being amplified. In some of these embodiments, the housing comprises at least one operably connected power source. In certain of these embodiments, the housing is operably connected, or connectable, to the RF tracking element and to the RF imaging element via at least one selectively connectable cable that comprises at least one operably connected resonant Radio-Frequency trap ("Bazooka Balun"-herein referred to as Balun). In some of these embodiments, the housing is operably connected, or connectable, to the MRI apparatus via at least one cable that comprises at least one operably connected Balun.

In some embodiments, the elongated probe is fabricated from at least one flexible material. In certain embodiments, the sheath and/or the elongated probe comprises at least one stylet. In certain embodiments, the elongated probe comprises at least one groove, wherein the RF tracking element and/or the RF imaging is at least partially disposed within the groove. In some embodiments, the elongated probe comprises at least one cavity, wherein at least one co-axial cable is at least partially disposed within the cavity and operably connected to the RF tracking element and/or the RF imaging and operably connected, or connectable, to the MRI apparatus. In some of these embodiments, the deflection mechanism comprises at least one tendon operably connected at least proximal to an end of the elongated probe that is insertable into the tissue and to a tension adjustment element operably connected to the handle, which tendon is at least partially disposed within the cavity and which tension adjustment element is configured to selectively effect deflection of the positioning of the portion of the elongated probe. In certain of these embodiments, the cavity is disposed substantially through a length of the elongated probe. In some of these embodiments, the elongated probe comprises at least one stylet. In certain of these embodiments, the elongated probe comprises a deflectable tube that comprises the cavity. In some embodiments, the elongated probe comprises at least one deflectable region that deflects when the deflection mechanism selectively deflects positioning of the portion of the elongated probe. In some of these embodiments, the deflectable region comprises at least one orifice disposed at least partially through the elongated probe. In certain of these embodiments, the orifice comprises at least one indentation disposed substantially perpendicular to a longitudinal axis of the elongated probe. In some of these embodiments, the orifice communicates with the cavity. In certain of these embodiments, the deflectable region comprises multiple orifices disposed at least partially through the elongated probe.

In some embodiments, the system includes at least a portion of at least one axial rotational control mechanism operably connected, or connectable, to the device. In some of these embodiments, the axial rotational control mechanism comprises at least one dial indicator operably connected to the elongated probe, which dial indicator indicates at least one rotational angle formed between at least a portion of the elongated probe and at least one template device when the elongated probe is inserted into the tissue. In certain of these embodiments, at least one dial is operably connected, or connectable, to the template device, which dial shows the rotational angle formed between the portion of the elongated probe and the template device when the elongated probe is inserted into the tissue.

In certain embodiments, the device includes at least two RF tracking elements operably connected to the elongated probe, which RF tracking elements are each operably connected, or connectable, to the MRI apparatus. In some embodiments, the RF tracking element comprises one or more micro-coils. In some embodiments, the RF tracking element and the RF imaging element are operably connected to the MRI apparatus. In certain embodiments, the RF tracking element comprises at least one antenna tuned, or tunable, to a magnetic resonance (MR) operational (Larmor) frequency. In some embodiments, the RF tracking element is configured to indicate the positions of the elongated probe at temporal rates of between about 10-50 frames per second.

In certain embodiments, the RF imaging element comprises one or more micro-coils. In some embodiments, the RF imaging element comprises at least one antenna tuned, or tunable, to a magnetic resonance (MR) operational (Larmor) frequency. In certain embodiments the RF imaging element comprises at least one outward-looking imaging array configured to provide outward-looking imaging. In certain embodiments the RF imaging element is configured to image one or more tissue regions surrounding a hole in the tissue that comprise a diameter of up to about 100 mm (e.g., about 10 mm, about 20 mm, about 30 mm, about 40 mm, about 50 mm, about 60 mm, about 70 mm, about 80 mm, about 90 mm, etc.) around the hole, when the elongated probe is inserted in the hole in the tissue. In some embodiments the RF imaging element is configured to image the tissue along a length of a hole in the tissue that extends up to about 100 mm (e.g., about 10 mm, about 20 mm, about 30 mm, about 40 mm, about 50 mm, about 60 mm, about 70 mm, about 80 mm, about 90 mm, etc.), when the elongated probe is inserted in the hole in the tissue.

In certain embodiments, the device includes at least one covering disposed around at least a portion of the sheath and/or the elongated probe. In some embodiments, the MRI apparatus comprises at least one MRI scanner. In some embodiments, the deflection mechanism is configured to selectively deflect positioning of at least a tip of the elongated probe. In certain embodiments, the device includes at least one collet adapter operably connected to the handle and at least one collect nut adjustably engaged with the collet adapter, which collet adapter and collet nut are configured to adjustably limit radial and/or axial displacement of the elongated probe and/or the sheath relative to the handle. In some embodiments, the instructions perform at least one MRI pulse sequence. In some embodiments, the device includes at least one display device operably connected to the controller, which display device is configured to display the positions of the elongated probe and the images of the elongated probe and/or the tissue in substantially real-time at least when the elongated probe is inserted into the tissue.

In some embodiments, the sheath and/or the elongated probe comprises at least one MRI compatible metal. In certain of these embodiments, the metal comprises at least one shape memory or super-elastic alloy. In some of these embodiments, the shape memory or super-elastic alloy comprises an alloy of nickel and titanium. In some of these embodiments, at least a portion of the sheath comprises an outer-diameter of between about 1 mm and about 5 mm. In some of these embodiments, the portion of the sheath comprises an outer-diameter of about 2.2 mm.

In certain embodiments, the sheath and/or the elongated probe comprises at least one conduit that comprises at least first and second openings, wherein the conduit is configured to convey one or more materials through the first opening and through the second opening, when the first opening is in communication with one or more material reservoirs and when the second opening is positioned at a selected location within or proximal to the tissue. In some of these embodiments, the conduit is disposed through at least a portion of the elongated probe. In some of these embodiments, the material reservoirs comprise one or more materials. In certain of these embodiments, the materials comprise one or more therapeutic agents.

In some embodiments, at least a portion of the elongated probe comprises an outer-diameter of between about 0.1 mm and about 5 mm. In certain of these embodiments, the portion of the elongated probe comprises an outer-diameter of about 1.5 mm. In certain embodiments, the elongated probe comprises a length capable of extending from the sheath of between about 1.0 mm and about 1000 mm. In some of these embodiments, the length of the elongated probe capable of extending from the sheath is 330 mm.

In certain embodiments, the deflection mechanism comprises at least one tendon operably connected at least proximal to an end of the elongated probe that is insertable into the tissue and to a tension adjustment element operably connected to the handle, which tension adjustment element is configured to selectively effect deflection of the positioning of the portion of the elongated probe.

In some of these embodiments, the tendon is fabricated from an alloy of nickel and titanium. In certain of these embodiments, the tension adjustment element comprises a rotary actuated nut operably connected to the tendon and a rotary knob that adjustably engages the rotary actuated nut. In certain of these embodiments, the device includes at least one tendon guide element operably connected to the handle, which tendon guide element limits the load on the sheath when tension applied to the tendon is increased.

In another aspect, the present disclosure provides a computer readable media comprising non-transitory computer-executable instructions which, when executed by at least one electronic processor perform at least: tracking one or more positions of an elongated probe of a magnetic resonance imaging (MRI) compatible tissue analysis device in substantially real-time at least when the elongated probe is inserted into at least one tissue. The tissue analysis device comprises: the elongated probe, at least one radio-frequency (RF) tracking element operably connected to the elongated probe, which RF tracking element is operably connected to at least one MRI apparatus, at least one RF imaging element operably connected to the elongated probe, which RF imaging element is operably connected to the MRI apparatus, at least one deflection mechanism operably connected at least to the elongated probe, which deflection mechanism is configured to selectively deflect positioning of the elongated probe, and at least one handle operably connected at least to the elongated probe. The instructions also perform capturing one or more images of the elongated probe and/or the tissue in substantially real-time at least when the elongated probe is inserted into the tissue.

In another aspect, the present disclosure provides a computer readable media comprising non-transitory computer-executable instructions which, when executed by at least one electronic processor perform at least: tracking one or more positions of an elongated probe of a magnetic resonance imaging (MRI) compatible tissue analysis device in substantially real-time at least when the elongated probe is inserted into at least one tissue. The tissue analysis device comprises: at least one sheath comprising at least one channel disposed at least partially therethrough; the elongated probe at least partially disposed and selectively movable within the channel of the sheath; at least one radio-frequency (RF) tracking element operably connected to the elongated probe, which RF tracking element is operably connected to at least one MRI apparatus; at least one RF imaging element operably connected to the elongated probe and/or the sheath, which RF imaging element is operably connected to the MRI apparatus; at least one deflection mechanism operably connected at least to the elongated probe, which deflection mechanism is configured to selectively deflect positioning of the elongated probe; and at least one handle operably connected at least to the sheath. The instructions also perform capturing one or more images of the elongated probe and/or the tissue in substantially real-time at least when the elongated probe is inserted into the tissue.

In another aspect, the present disclosure provides a method of analyzing tissue. The method includes positioning a magnetic resonance imaging (MRI) compatible tissue analysis device substantially proximal to at least one tissue, which tissue analysis device comprises: at least one elongated probe, at least one RF tracking element operably connected to the elongated probe, which RF tracking element is operably connected to at least one MRI apparatus, at least one RF imaging element operably connected to the elongated probe and/or the sheath, which RF imaging element is operably connected to the MRI apparatus, at least one deflection mechanism operably connected at least to the elongated probe, and at least one handle operably connected at least to the elongated probe. The method also includes inserting at least a portion of the elongated probe into the tissue, tracking one or more positions of the elongated probe in substantially real-time using at least the RF tracking element and the MRI apparatus, and capturing one or more images of the elongated probe and/or the tissue in substantially real-time using at least the RF imaging element and the MRI apparatus, thereby analyzing the tissue.

In another aspect, the present disclosure provides a method of analyzing tissue. The method includes positioning a magnetic resonance imaging (MRI) compatible tissue analysis device substantially proximal to at least one tissue, which tissue analysis device comprises: at least one sheath comprising at least one channel disposed at least partially therethrough; at least one elongated probe at least partially disposed and selectively movable within the channel of the sheath; at least one RF tracking element operably connected to the elongated probe, which RF tracking element is operably connected to at least one MRI apparatus; at least one RF imaging element operably connected to the elongated probe and/or the sheath, which RF imaging element is operably connected to the MRI apparatus; at least one deflection mechanism operably connected at least to the elongated probe; and at least one handle operably connected at least to the sheath. The method also includes inserting at least a portion of the elongated probe into the tissue, tracking one or more positions of the elongated probe in substantially real-time using at least the RF tracking element and the MRI apparatus, and capturing one or more images of the elongated probe and/or the tissue in substantially real-time using at least the RF imaging element and the MRI apparatus, thereby analyzing the tissue.

In some embodiments, the method further includes selectively deflecting at least one position of the elongated probe using the deflection mechanism. In certain embodiments, the method includes capturing the images of one or more tissue regions surrounding a hole in the tissue that comprise a diameter of up to about 100 mm around the hole, when the elongated probe is inserted in the hole in the tissue. In some embodiments, the method includes capturing the images of the tissue along a length of a hole in the tissue that extends up to about 100 mm, when the elongated probe is inserted in the hole in the tissue. In certain embodiments, the method includes the sheath and/or the elongated probe comprises at least one conduit that comprises at least first and second openings, wherein the first opening is in communication with one or more material reservoirs that comprise one or more materials and wherein the method comprises conveying the materials through the first opening and the conduit from the material reservoirs and out of the second opening within or proximal to the tissue and/or conveying the materials and/or one or more samples through the second opening and the conduit from or proximal to the tissue and out of the first opening into the material reservoirs. In certain embodiments, the device comprises at least a portion of at least one axial rotational control mechanism operably connected to the elongated probe and wherein the method further comprises indicating at least one rotational angle formed between at least a portion of the elongated probe and at least one template device that is positioned at least proximal to the tissue.

BRIEF DESCRIPTION OF THE DRAWINGS

The accompanying drawings, which are incorporated in and constitute a part of this specification, illustrate certain embodiments, and together with the written description, serve to explain certain principles of the methods, devices, kits, systems, and related computer readable media disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

FIG. 1 schematically depicts a miniature Baluns (MBalun) mounted on an elongated probe (shown as a nitinol tube) according to one exemplary embodiment (panel A) and images of data from a simulation using a conducting tube without MBaluns as well as another simulation using a conducting tube with MBaluns (panel B).

FIG. 2C shows a simulated lobe pattern created by the RF tracking element from FIG. 2B.

FIG. 3 is a flow chart that schematically depicts exemplary method steps according to some aspects disclosed herein.

FIG. 10 schematically shows a cross-section view of a device handle assembly 1000 that illustrates the relative positioning of (1) a collet nut 1001, (2) a collet adapter 1003, (3) a constraining collet 1005, (4) an extruded guide 1007, (5) a Nitinol tendon 1009, (6) a rotary actuated nut 1011, and (7) a rotary knob 1013 according to one exemplary embodiment.

FIG. 11 (panels A and B) schematically shown portions of an elongated element 1100 according to one exemplary embodiment.

DEFINITIONS

Figure 2A:
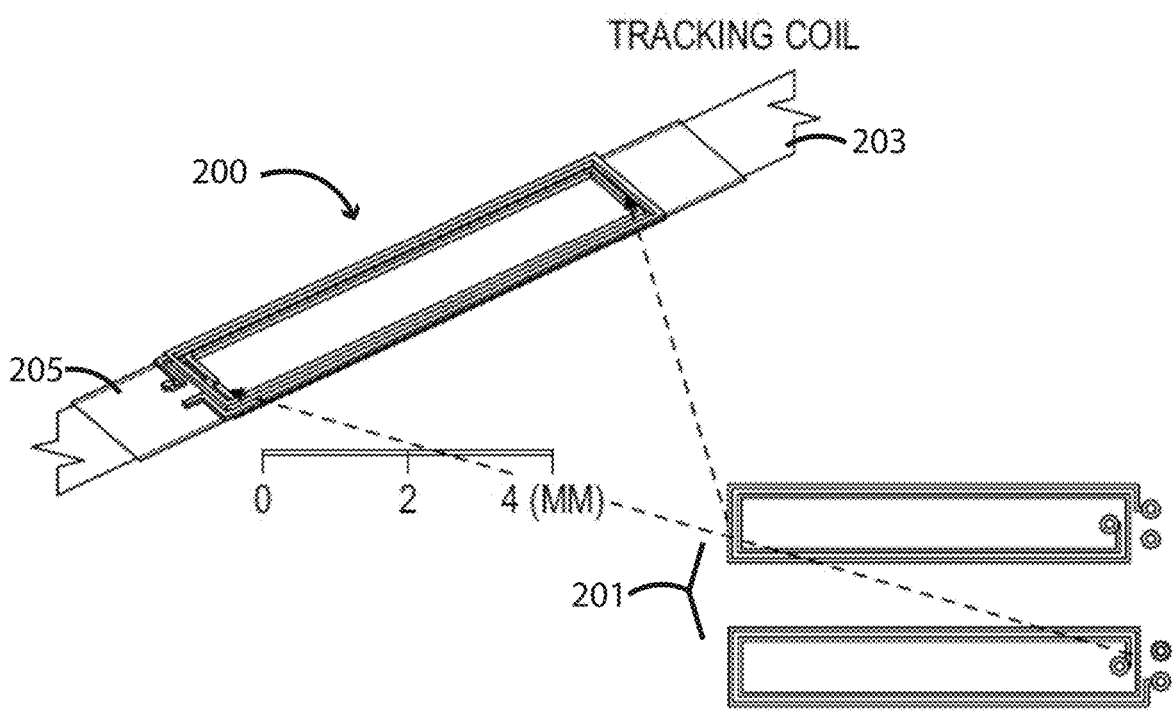
FIG. 2A schematically shows an RF tracking element 200 from a perspective view according to one exemplary embodiment.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this disclosure pertains. In describing and claiming the methods, systems, and component parts, the following terminology, and grammatical variants thereof, will be used in accordance with the definitions set forth below.

About: As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Subject: As used herein, "subject" refers to an animal, such as a mammalian species (e.g., human) or avian (e.g., bird) species. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual that is in need of therapy or suspected of needing therapy. The terms "individual" or "patient" are intended to be interchangeable with "subject." For example, a subject can be an individual who has been diagnosed with having a respiratory disease, disorder, or condition, is going to receive a therapy for a respiratory disease, disorder, or condition, and/or has received at least one therapy for a respiratory disease, disorder, or condition.

DETAILED DESCRIPTION

To evaluate the state of a region within human tissue, such as whether it contains cancer cells or necrotic cells, whether it is sufficiently perfused, whether there is inflammation present, and the like, the conventional tool is to penetrate the tissue, excise a sample volume of the tissue and send it to pathology for analysis. Similar demands occur when there is interest in understanding the response of tissue to radiation or to chemical or biologics infusion, where, again, the conventional tool is to biopsy the tissue. An alternative to biopsy is to evaluate the state of tissue in-situ without removing a sample of the tissue from a given subject. This is performed, for example, within the vascular system (blood vessels and heart chambers) using tools such as Optical Coherence Tomography (OCT) and Intravascular Ultrasound (IVUS), or within the Gastro-Intestinal voids using video transmitting "pills" or endoscopes. The advantages of these tools are in the ability to: (i) perform scans that span extended distances (and volumes), rather than at sparse discrete locations, (ii) perform the analyses quickly, in order to provide rapid reports and visualize dynamic processes (such as perfusion/diffusion of various therapeutic agents into the tissue), and (iii) minimize the amount of tissue destruction due to the diagnosis.

Recent innovations in magnetic resonance imaging (MRI) demonstrate the feasibility of obtaining sub-millimeter device positional localization by mounting magnetic resonance (MR)-tracking micro-coils on the interventional device [Wang et al. "Evaluation of an active magnetic resonance tracking system for interstitial brachytherapy," Medical physics, 42:7114-7121 (2015)] and using an MR-tracking sequence to find them. In addition, high-resolution (~0.1 mm scale) MR-imaging can be enabled by millimeter-size imaging coils that are brought close to the target tissue. These promising findings indicate the potential to "virtually" characterize the tissue property from MR images. In addition, an interventional stylet integrated with MR-tracking coils was recently developed for brachytherapy of gynecological cancer [Chen et al., "Design and fabrication of MR-tracked metallic stylet for gynecologic brachytherapy," IEEE/ASME Transactions on Mechatronics, 21:956-962 (2015)]. Two tracking coils were integrated into the custom-designed stylet to provide fast positioning and stylet tip tracking (~30 Hz update rate) within the MRI scanner. However, it is difficult to control the straight stylet to reach a wide range of workspace due to the limited degrees of freedom. This results in the need for multiple insertion and retraction trials for the stylet to hit the desired target, resulting in increased tissue disruption and damage, as well as extending the length of the procedure.

Accordingly, in certain aspects, the present disclosure provides a deflectable elongated probe (e.g., a stylet, etc.) that carries both tracking and imaging coils to provide focal high resolution tissue characterization at the same time (i.e., in real-time) as holes are punctured into a given tissue type, such as a tumor in order to insert localized interstitial radiation (e.g., brachytherapy) sources in some embodiments. The methods disclosed herein address the limitations of, for example, conventional OCT or IVUS methods (e.g., short visualization depth and the need for vascular access) by carrying the imaging coil close to the target directly. As compared to conventional biopsy, for example, the approaches disclosed herein typically do not involve tissue removal. These and other aspect are described further herein.

In some embodiments, the devices and related aspects of the present disclosure are used to provide tissue definition within soft-tissue that cannot be accessed entirely through the orifices of a subject's body or via the vascular system. There are some conventional diagnostic tools (or methods) that penetrate a portion of the distance from the outside the body to the desired target(s) via an orifice, and then go the rest of the way by perforating tissue. In certain applications, the devices and systems described herein use a similar approach, while employing different sensors, among other distinctions. In certain embodiments, for example, the devices and systems described herein combine (1) navigational and localization capabilities of magnetic resonance (MR)-tracking methods, which provide at least sub-millimeter precision location information, (2) high-resolution (~0.1 mm scale) magnetic resonance imaging (MRI) with high a contrast to noise ratio (CNR), which is enabled by millimeter-size imaging coils that are positioned close to the target tissue, (3) multiple contrast (e.g., hypoxia, fibrosis, oxygenation, edema, etc.) imaging which are enabled by MRI methods disclosed herein that can be performed quickly due to the high CNR afforded by the high-sensitivity MRI receiver arrays that are brought very close to the target tissue, (4) a manually-controlled elongated probe or stylet deflection mechanism to enhance the needle dexterity, which improves the targeting accuracy and reduces the multiple trials of inserting and retracting the tool that were previously necessitated in order to hit the target tissue location. In other exemplary aspects, the devices disclosed herein are also used to perform: (a) methods (using lumens, injection ports, material reservoirs, etc.) to insert materials (such as gases, liquids, solids and/or gels) into tissues of interest, (b) methods of non MRI-based tissue evaluation (such as optical imaging and ultrasound imaging) or combined MRI-based and non-MRI based diagnosis (such as, MR elastography and the like), (c) methods to destroy tissue (such as thermal or cryogenic ablation, irreversible electroporation, etc.), and (d) methods to physically excise tissue and allow its removal (i.e., perform MRI-guided spatial-localized biopsy).

In exemplary embodiments, the devices disclosed herein integrate various components or features. For example, the devices typically includes a mechanically-flexible elongated probe (e.g., a metallic (nitinol-based) stylet in some embodiments) that is used to puncture relatively hard soft tissue and to navigate to desired locations within the tissue. The devices also typically include MR tracking micro-coils that are placed in grooves on, for example, the distal end of the stylet and indicate the location and orientation of the elongated probe or stylet tip at temporal rates of about 15-30 frames per second, in certain embodiments, as the elongated probe is navigated through the tissue being analyzed. These micro-coils are typically implemented using a design that optimizes the field outside the surface of the elongated probes that involves the use of thin multilayer (e.g., 3-layer) antenna design that has a thickness of only about 0.25 millimeters. This maintains a thin elongated probe profile, which does not create large holes in a subject's body upon insertion. The micro-coils are generally tuned and matched to the MRI Larmor frequency on the MR-tracking flexible printed circuits themselves (e.g., by employing embedded dielectric layers as capacitors in certain embodiments) so as to perform high CNR MR-tracking despite the reduced dimensions.

The devices and methods disclosed herein also generally permit a clinician or a robot to deflect the tip of the elongated probe remotely, for example, from outside the body, using a tendon or pull-wire mechanism in some embodiments. The autonomous deflection of the elongated probe (e.g., stylets, needles, or the like) can be achieved, for example, by connecting the actuation tendon wire to an MRI compatible actuator, an active lead screw, or a tendon driven mechanism, etc. To achieve the robotic insertion of the elongated probe (e.g., stylets, needles, or the like), the hardware structure can be mounted on the one degree of freedom MRI compatible linear translation platform or a multiple degrees of freedom MRI compatible robot. In certain embodiments, the mechanism to deflect the tip of elongated probes is disposed at least partially within a "biopsy gun" structure.

The devices disclosed herein also typically utilize small thickness (~0.25 mm) MR-imaging coils mounted on a structure (e.g., a sheath) that is placed immediately behind (i.e. more proximal to) the MR-tracking coils. In some embodiments, these imaging coils use a thin multilayer (2-layer antenna) design that has a thickness of only 0.25 millimeters, leaving the tip with a thin outer diameter (~2.2 millimeter), so that the device does not create a large hole in a given subject's body upon insertion. The imaging coils are generally tuned and matched to the MRI frequency on the flexible printed circuits themselves (e.g., by employing embedded dielectric layers as capacitors in certain embodiments) so as to perform high CNR imaging despite their reduced dimensions. These imaging coils are typically constructed to function as outward-looking coils, which employ the image radio-frequency (RF) magnetic-field properties of metallic surfaces, in order to image regions of about 12-24 mm diameter, along a length of about 10-20 millimeters, around the holes created by elongated probe punctures. In certain applications, regions of about a 5 mm diameter around the inserted elongated probes have disturbed properties due to the puncturing process (e.g., different perfusion and diffusion properties due to mechanical tearing).

In certain embodiments, the devices disclosed herein are integrated with MR-tracking pulse sequences that provide the high frame rates (and high temporal-resolutions) and high spatial-resolution localizations while navigating the elongated probes of the devices through tissue, as well as with a set of optimized MRI pulse sequences that allow for rapid imaging of a set of MR-imaging contrasts that provide the tissue properties.

Figure 2B:
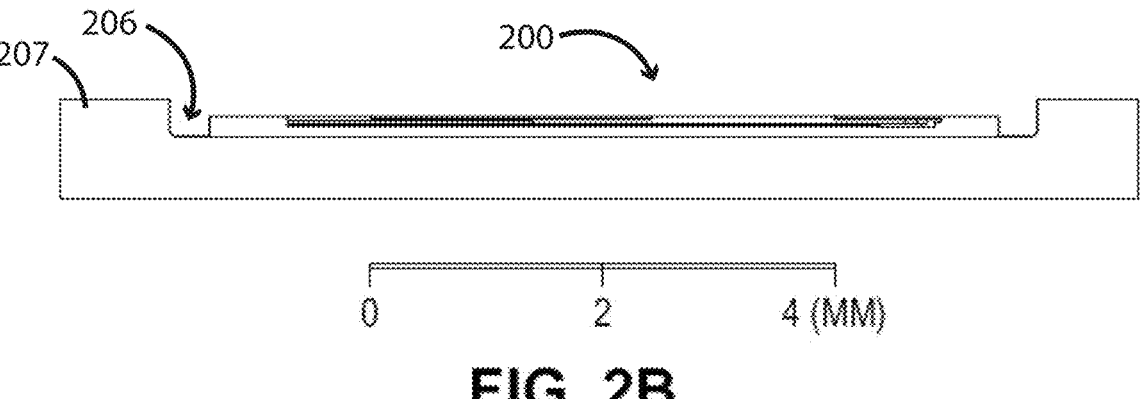
FIG. 2B schematically depicts the RF tracking element 200 from FIG. 2A disposed in a groove 206 of an elongated probe 207 from a side view according to one exemplary embodiment.

In some embodiments, when the length of an elongated probe of a given device exceeds a quarter of the RF wavelength (e.g., ~30 cm at 1.5 Tesla), one or more miniaturized resonant floating RF traps (e.g., miniature Baluns (MBaluns)) are operably connected to the elongated probe, for example, to further make the device MR safe by preventing or minimizing heating of the surroundings during use. FIG. 1 schematically depicts a miniature Baluns (MBalun) (RF imaging element) mounted on an elongated probe (shown as a nitinol tube) according to one exemplary embodiment (panel A) and images of data from a simulation using a conducting tube without MBaluns as well as another simulation using a conducting tube with MBaluns (panel B). MBaluns that are optionally adapted for use in the devices of the present disclosure are further described, for example, in Alipour et al., "MRI Conditional Actively-Tracked Metallic Electrophysiology Catheters and Guidewires with Miniature Tethered Radio-Frequency Traps: Theory, Design and Validation," IEEE Trans Biomed Eng. (Early Publication), 1-15 (2019) and International Application No. PCT/US2018/047157, filed 21 Aug. 2018, which are each incorporated by reference in their entirety. In certain embodiments, the directionality of the RF imaging elements and the depth of penetration of the imaging into the surrounding tissue can altered by varying slightly the shape of, for example, the (a) the underlying metallic tubes (e.g., shaping them as cones rather than as cylinders, etc.), (b) the thickness and shape of the insulator(s) (e.g., shaping them as reversely oriented cones, etc.), and/or (c) varying the shape of the RF imaging elements (e.g., using 3 coils, each with a larger width, instead of 4 coils or the like). To further illustrate, FIGS. 2A-2C illustrate an exemplary RF tracking coil 201 and a simulated lobe pattern created by the RF tracking coil placed on a metallic surface 203 with an insulator substrate 205 positioned below the coil.

To further illustrate, FIG. 3 is a flow chart that schematically depicts an overview of exemplary method steps of using the devices and systems provided in the present disclosure. As shown, method 300 includes inserting the elongated probe of the MRI compatible tissue analysis device into the selected tissue of a subject (step 302). Method 300 also includes tracking positions of the elongated probe in substantially real-time using the RF tracking element and the MRI scanner (step 304). In addition, method 300 also includes capturing images of the elongated probe and/or the selected tissue (e.g., at a distance surrounding the inserted elongated probe) in substantially real-time using the RF imaging element and the MRI scanner (step 306). Typically, this process involves (a) moving the elongated probe a given distance (e.g., a few millimeters (mm)) at a time, and then (b) performing a series of imaging sequences, which depend on the information desired by the clinician or other user, and then repeating steps (a, b) multiple times to obtain the desired images and other data.

Figure 4A:
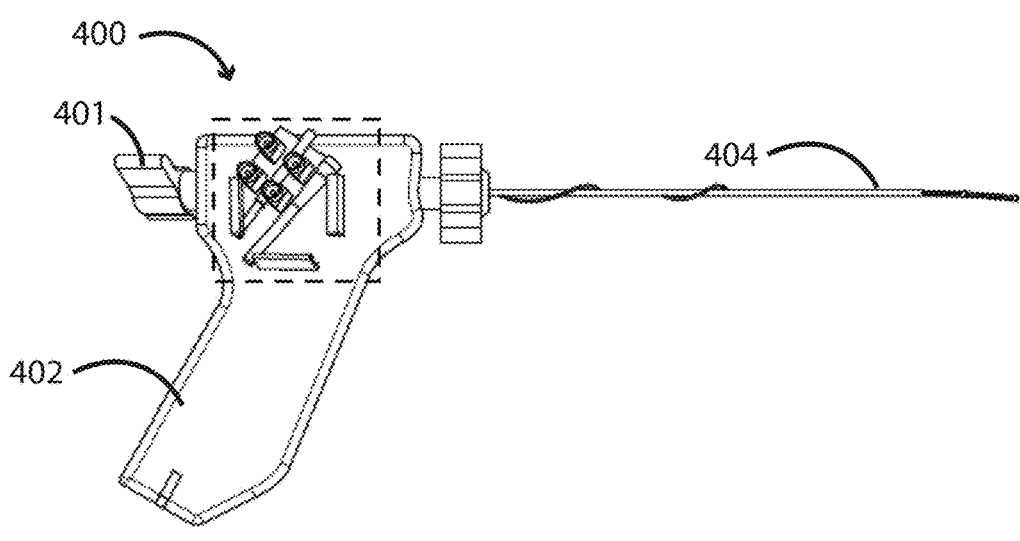
FIG. 4 (panels A and B) schematically shows side views of an exemplary MRI compatible tissue analysis device 400 according to some aspects disclosed herein. As shown in panel A, coaxial "Bayonet Neill-Concelman" (BNC) connectors 401 are disposed on an outer surface of the device handle 402 for connecting the imaging array to an MRI apparatus (see the dashed rectangle in panel A). As also shown, the elongated probe 404 (e.g., a stylet) can be accurately deformed or deflected (see the dashed rectangle around the tip 403 in panel B) by input from the control handle 402 (see the dashed rectangle around the handle in panel B).
Figure 4B:
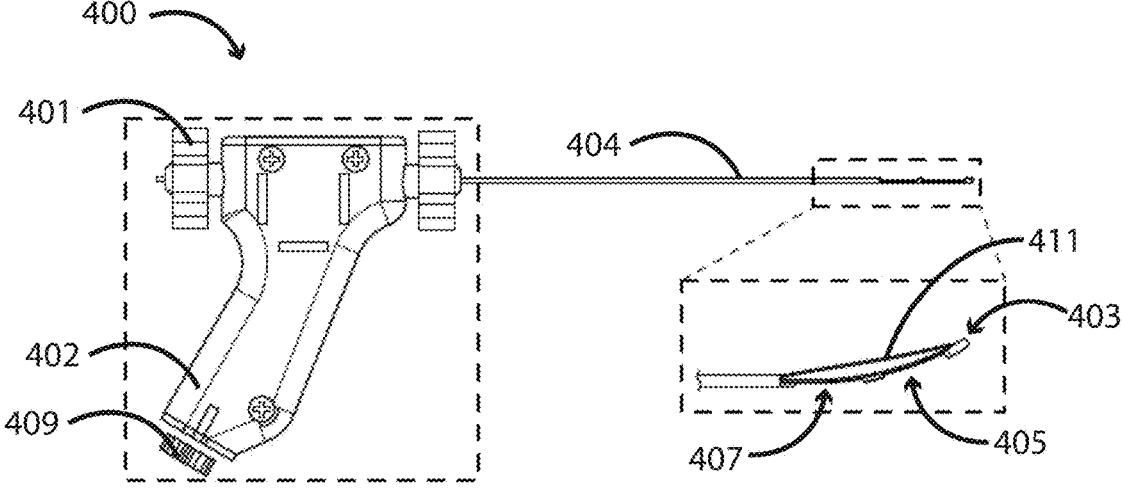

In various embodiments, the present disclosure provides devices, kits, systems, and computer readable media for in-situ tissue imaging and analysis. For example, the minimally invasive devices or assemblies disclosed herein enable (i) dexterous motion, (ii) real-time position tracking, and (iii) high-resolution tissue imaging, among other aspects. Typically, these devices or assemblies are designed to consistently deflect and maintain the deflection of the component elongated probes (e.g., stylets having 1.5 mm outer-diameter and 330 mm lengths in certain exemplary embodiments), while incorporating the micro tracking and imaging coils. In addition, these devices generally maintain sufficient rigidity and only have localized deflection at the tip of the elongated probes (e.g., stylets, needles, or the like) in some of these embodiments. An exemplary magnetic resonance imaging (MRI) compatible tissue analysis device is schematically shown in FIG. 4. In certain embodiments, dexterous elongated probe deflection is accomplished through a tendon-driven mechanism, where the radial motion of a threaded knob 409 induces tendon 411 tension and deflection of the elongated probe 404. A sufficiently rigid outer sheath, placed concentric to the stylet, is typically used to constrain the deflecting part of the elongated probe 404 to the segment which protrudes out of the sheath. In some embodiments, an imaging array of micro-coils are mounted around the circumference of the outer sheath of the devices to provide outward-looking imaging. In certain embodiments, tracking micro-coils are mounted within grooves (e.g., machined grooves or the like) in a distal end of the elongated probe 404 to provide tracking of the distal location and orientation of the distal elongated probe.

Elongated Probe Design

Figure 5:
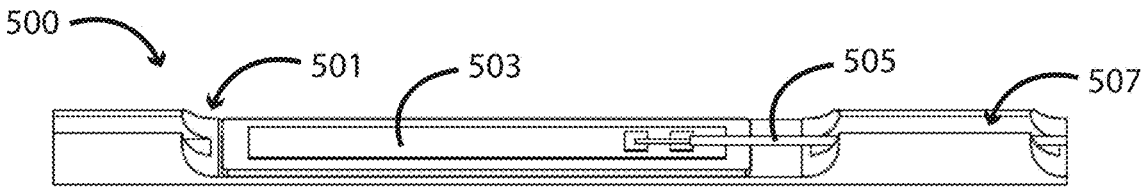
FIG. 5 schematically depicts a perspective view of a distal end of an elongated probe 500 (e.g., a stylet) according to one exemplary embodiment. The micro-coils 503 are mounted to the machined grooves 501 as shown in the image. The co-axial cables 505 are soldered to the micro-coil and guided through the channel or cavity 507 as shown in the image.

Although essentially any other flexible or deflectable MRI compatible material is optionally used, the elongated probe is fabricated from an alloy of nickel (Ni) and titanium (Ti) (e.g., Nitinol (commercially available from the Memry Corp. (Bethel, CT, USA)) or the like) in certain embodiments. Nitinol, for example, possesses super-elastic properties, permitting a large elastic deflection without plastic deformation, while also being MRI compatible [Chen et al., "MR-conditional steerable needle robot for intracerebral hemorrhage removal," International journal of computer assisted radiology and surgery, 14:105-115 (2019)]. In order to incorporate the RF tracking elements (e.g., tracking coils) into the elongated probe (e.g., stylet) design, flat surfaces are machined in the distal end of the elongated probe in some embodiments to permit the placement of the coils. FIG. 5 schematically shows the machined grooves 501, as well as the coil 503 placement according to one exemplary embodiment. However, due to the inherently difficult nature of machining Nitinol using traditional cutting methods, in some embodiments these surfaces are machined using a process known as Electric Discharge Machining (EDM), which is the process of removing material by using an electrode to erode an electrically conductive material [Fleming, Build a Pulse EDM Machine: The Next Generation. Fayetteville, AR.: Fleming Publications (2011)]. The distal 405 and proximal 407 tracking-coil grooves depicted in the embodiment shown in, for example FIGS. 4 and 5, start 6 mm and 22 mm away, respectively, from the distal end of the elongated probe, with the cuts extending approximately 12.7 mm, with a depth of 0.68 mm, which allows enough space for the coil 503 and the micro-axial cables 505 attached to it to remain within the profile of the stylet's diameter, preventing damage to the coils or the cables. To prevent damage to the co-axial cables running the MR signal along the length of the stylet, a channel or cavity 507 is optionally cut straight along the longitudinal axis across the length of the elongated probe (e.g., a stylet or the like) with a depth of 0.4 mm. In some embodiments, a covering (e.g. a flexible, MRI compatible, medical grade elastomeric material or the like) is disposed around at least a portion of the elongated probe to protect the RF tracking elements, the RF imaging element, and the subject during use of the device.

Deflection Tendon Attachment Method

In some embodiments, a tendon-based deflection mechanism is used to selectively induce deflection of the elongated probe tip. Although other diameters are optionally used, in some embodiments the tendon is between about 0.1 mm and 3.0 mm in diameter (e.g., 0.381 mm in diameter, etc.). In certain of these embodiments, the tendon is also made of Nitinol. Although Nitinol is an MRI compatible material, it can present certain challenges with respect to attaching the tendon to the distal end of the elongated probe: (i) the soldered joint should be sufficiently compact, and (ii) the joint cannot break under unforeseen loads. To address these challenges, soldering is used to attach the tendon to the elongated probe in some embodiments, as depicted, for example, in FIG. 6. In these embodiments, in order to remove oxides from the surfaces, the elongated probe 600 and tendon interfacing surfaces are optionally roughened with, for example, 400 grit sandpaper, cleaned with 91% isopropyl alcohol, and then prepped with Indium Corporation Flux #2, an acid-based flux formulated for soldering to Nitinol (commercially available from Indium Corporation, Chicago, IL, USA). The joint is then optionally soldered using Indalloy solder #121 (96.5Sn 3.5Ag, 0.030 in (0.762 mm) solder wire) at 435° C. To ensure the strength of the soldered joint, a region extending about 3 mm from the distal end of the elongation probe is utilized for the soldering interface in some embodiments.

Figure 6:
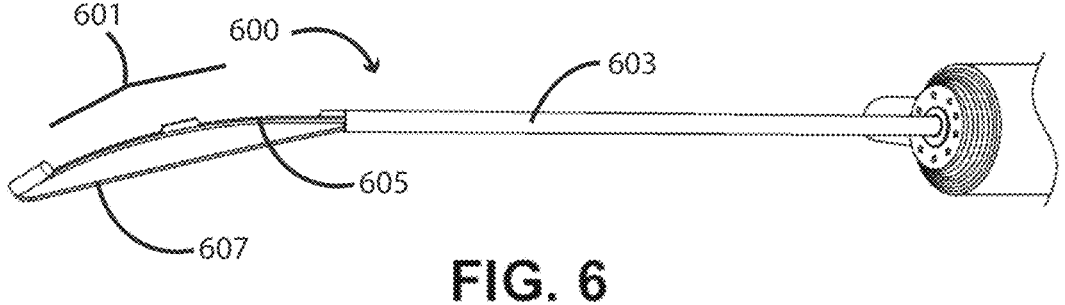
FIG. 6 is an image of an elongated probe tip 600 being deflected under an applied tendon force from a side view according to one exemplary embodiment.

In order to limit the deflection near the elongated probe tip 601, and to maintain rigidity of the remaining length of the elongated probe 600, a concentric metal sheath 603 (e.g., in the range of about 1 mm to 5 mm outer diameter (e.g., 2.2 mm outer diameter)) is typically placed approximately 12 mm behind the proximal RF tracking element 605 (e.g., an MR-tracking coil) as shown in FIG. 6 in some embodiments. This sheath 603 provides a rigid outer shell, which remains statically straight regardless of the dynamic tension applied by the tendon. The super-elastic material Nitinol is optionally used as the sheath material as well.

In some embodiments, a groove on the underside of the elongated probe is machined similar to the top side grooves as described herein, to recess the tendon 607 partially into the elongated probe 600, thereby reducing the overall dimension. Additionally, the elongated probe tip 601, tendon 607, and coils are also optionally surrounded by a compliant concentric tube or covering that allows deflection. This compliant tube acts as a safeguard for the coils, while also constraining the tendon to the contour of the tube to prevent the divergence of the tendon from the elongated probe as shown in FIG. 6.

MRI Tracking and Imaging Coil Integration

Figure 7:
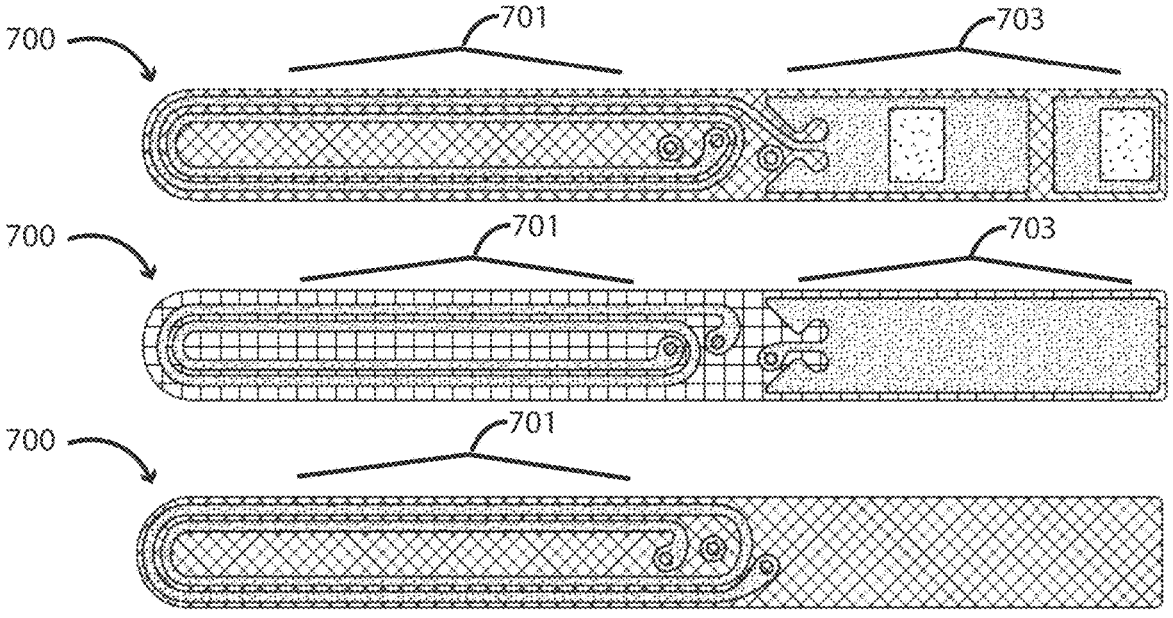
FIG. 7 schematically shows the individual layers 700 of a three layer active tracking coil according to one exemplary embodiment. The left side of the image are the antennas 701, and the right side are the embedded parallel and series capacitors 703, which are used to tune and match the circuit for work at 63.8 MHz (1.5 T) [50 Ohms impedance at 1.5 T].
Figure 8:
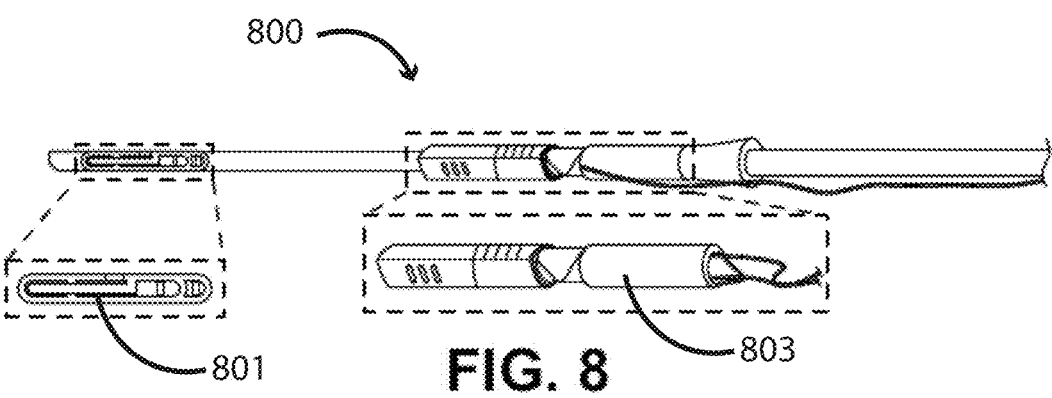
FIG. 8 is an image showing RF tracking elements 801 (e.g., small tracking micro-coils) and an RF imaging element 803 (e.g., imaging micro-coils) attached using fast-curing adhesive after a tendon is soldered to an elongated probe 800 (e.g., a stylet) and coaxial cables are soldered to the micro-coils according to one exemplary embodiment.

The RF tracking elements (e.g., MR-Tracking micro-coils) indicate the location of the elongated probe tip at temporal rates of about 10-50 frames per second (e.g., about 15, about 20, about 25, about 30, about 35, about 40, or about 45 frames per second) as it is navigated through the tissue in certain embodiments. The micro-coils are typically implemented using a design that optimizes the field outside the metallic surface of the elongated probes (e.g., stylets). In some embodiments, this is accomplished by using a thin multilayer (3-layer antenna) design that has a thickness of only 0.25 mm. FIG. 7 schematically shows the individual layers of a three layer active tracking coil according to one exemplary embodiment. In some embodiments, the micro-coils used 46 AWG co-axial cables (Ø0.13 mm), which are soldered to the micro-coil pads. Once the co-axial cables are soldered to the micro-coils, the micro-coils are typically attached to the elongated probe using, for example, fast-curing adhesive. This step is generally conducted after the soldering of the tendon to the elongated probe to prevent heat damage to the coils. The micro-coaxial cables (Ø0.13 mm) are then typically routed along the channel or cavity machined into the elongated probe's shaft as described herein. As the micro-coaxial cables were routed, their position is locked in place by a quick curing adhesive in key locations to maintain their position until thin-walled heat shrink tubing can be used to constrain and protect the micro-coaxial cables in some embodiments. FIG. 8 shows the micro tracking coils 801 and their corresponding soldering pads.

Figure 9:
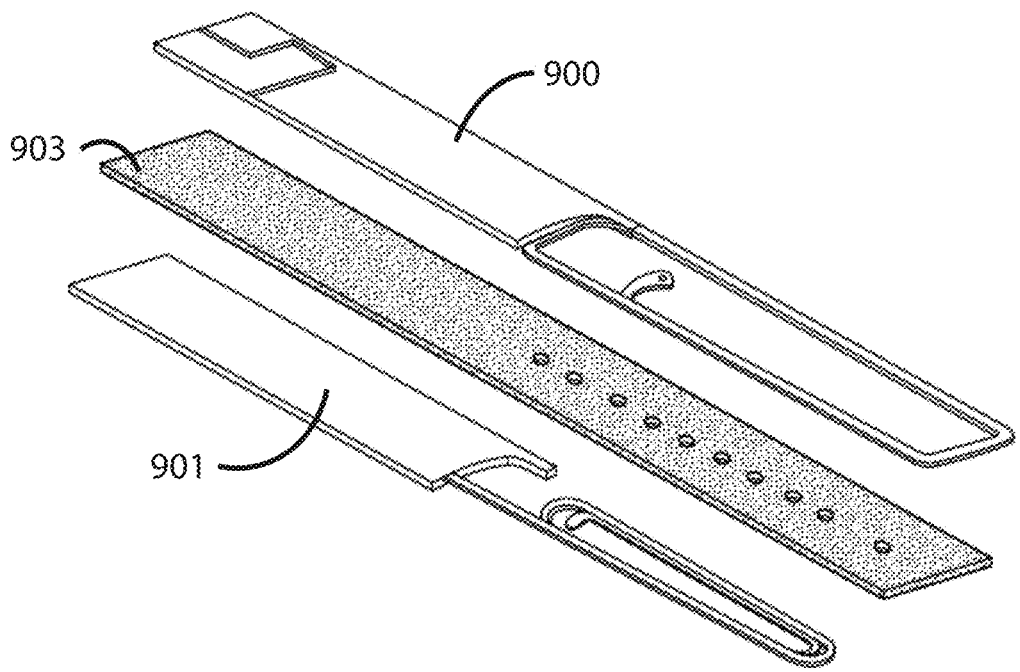
FIG. 9 is a diagram of two layer imaging coils 900 and 901 that are separated from metallic surfaces with an electrical insulator 903 of about 0.2 mm thickness according to one exemplary embodiment.
Figure 12:
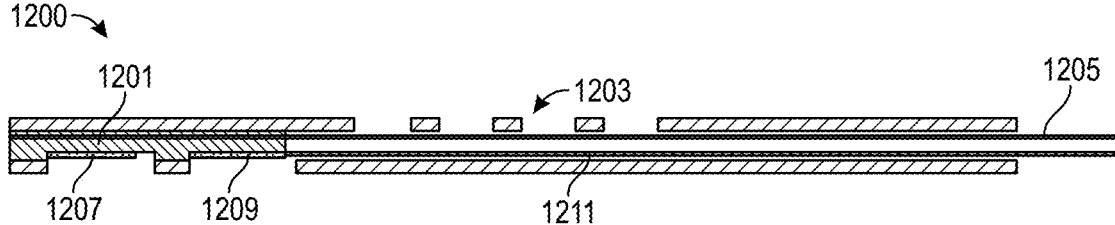
FIG. 12 schematically depicts an elongated probe from a cross-sectional side view according to one exemplary embodiment.
Figure 13:
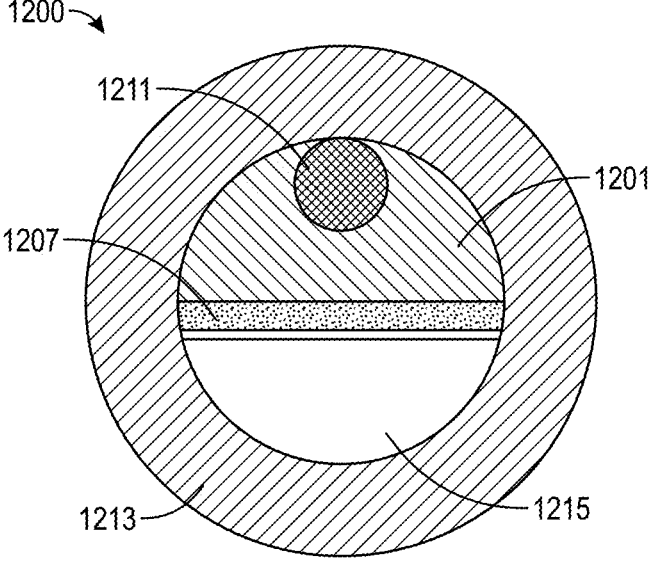
FIG. 13 schematically shows the elongated probe from FIG. 12 from a cross-sectional front view.
Figure 14:
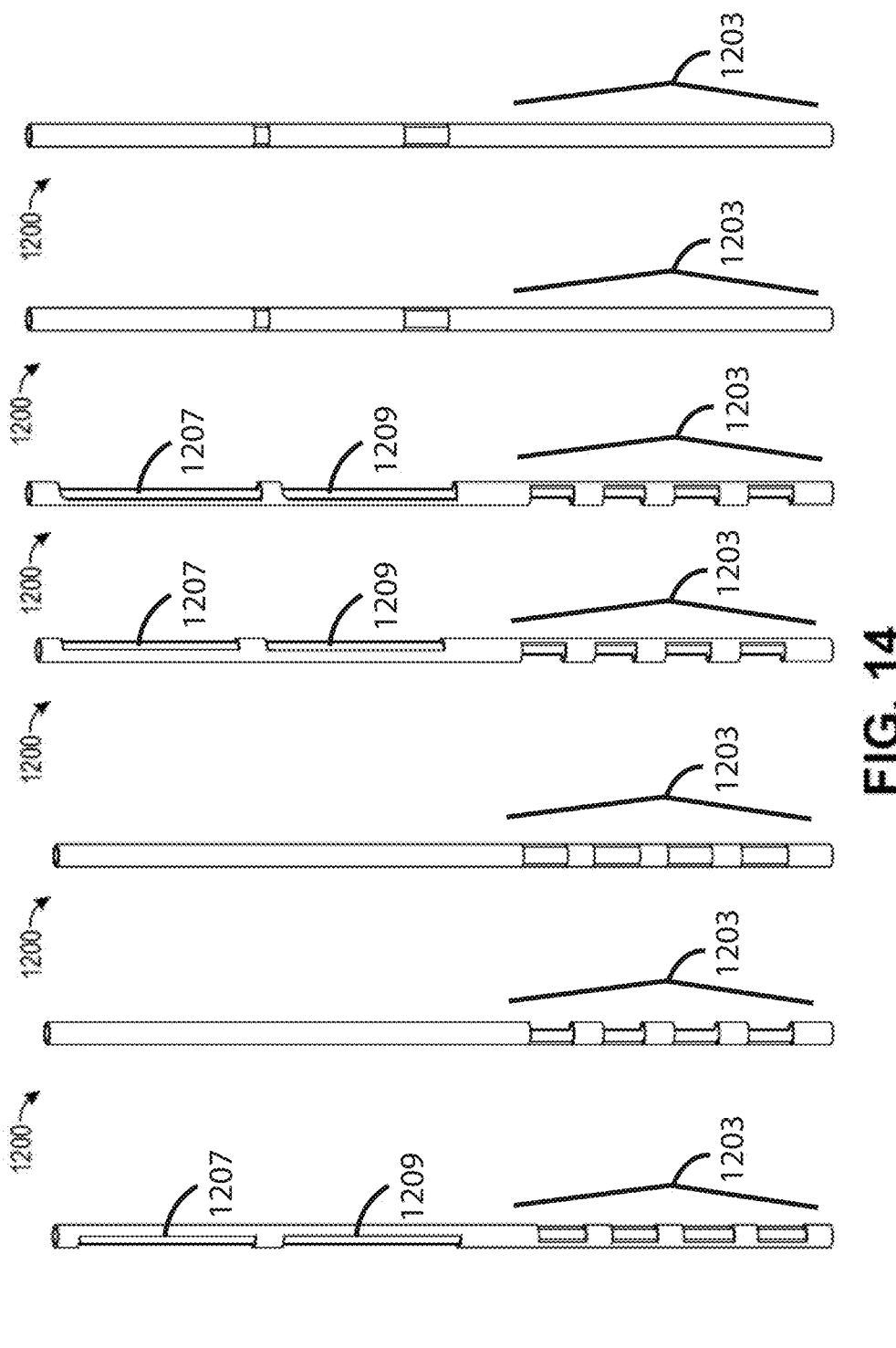
FIG. 14 (panels A-G) schematically show the elongated probe 1200 from FIG. 12 from various views.
Figure 15:
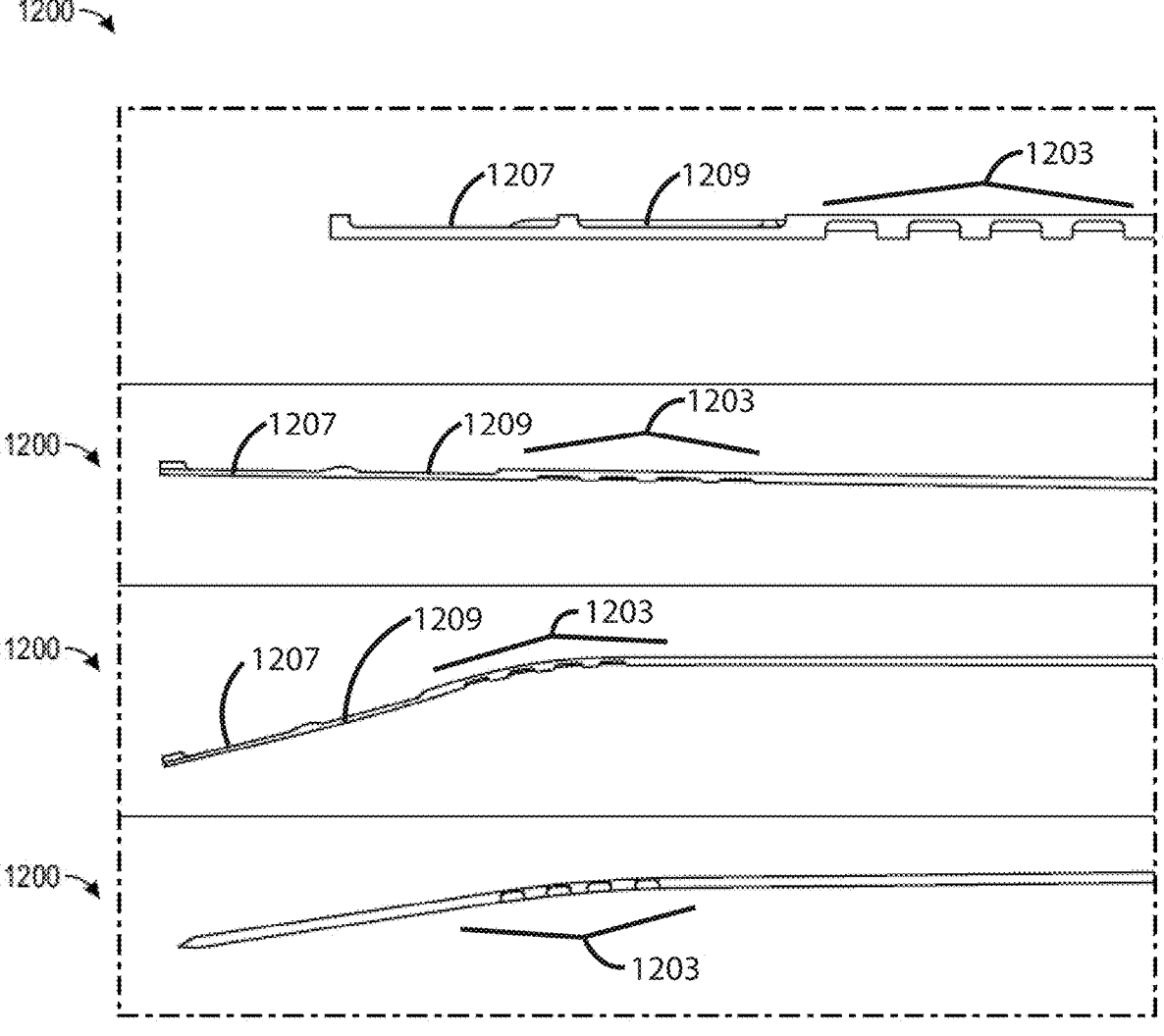
FIG. 15 (panels A-D) schematically show the elongated probe 1200 from FIG. 12 from various views.

In some embodiments, RF imaging elements (e.g., MR-imaging coils) are soldered to the 42 AWG co-axial cables in a similar manner to the RF imaging elements (e.g., MR-tracking coils) described herein. In some of these embodiments, the small thickness (~0.25 mm) imaging coils are mounted to the outer sheath. These imaging coils typically use a thin multilayer (2-layer antenna) design that have a thickness of only 0.25 mm, leaving the tip with a thin outer diameter (~2.2 mm), so that the device does not create a large puncture in the body of a subject during use. FIG. 9 is a diagram of two layer imaging coils 900 and 901 that are separated from metallic surfaces by about 0.2 mm according to one exemplary embodiment. Similar to certain embodiments of the tracking coils described herein, these exemplary imaging coils are tuned and matched using embedded capacitors. In some embodiments, these imaging coils are especially constructed in order to work as outward-looking coils, which employ the image Radio-Frequency (RF) magnetic-field properties of metallic surfaces, in order to image regions of about a 12-24 mm diameter, along a length of about 10-20 millimeter, around the holes created by the elongated probe puncture. The imaging coil construction is attached to the outer surface of the distal end of the outer sheath using fast-curing adhesive in some embodiments. The imaging coil array construction, as well as its placement with respect to the stylet, are shown in FIG. 7 according to one exemplary embodiment. RF imaging and tracking elements that are optionally used or adapted for use with the devices and systems disclosed herein are also described in, for example, International Application No. PCT/US2019/022460, filed 15 Mar. 2019, which is incorporated by reference in its entirety.

Control Handle and Deflection Mechanism

In certain embodiments, the device control handle is designed so that; (i) it can fit ergonomically in the hand of the user, (ii) it prevents axial and radial displacement of the elongated probe and sheath relative to the handle, and/or (iii) incorporates a deflection mechanism that resists elastic relaxation and substantially maintains a constant deflection. To accomplish design feature (i), the handle utilizes nylon flathead screws and a reciprocating threaded hole in the handle assembly to provide a low profile clamping force to hold the two halves of the handle assembly together in some embodiments. This prevents undesired extrusions protruding out from the smooth tangent surfaces of the handle. The handle is optionally fabricated from essentially any MRI compatible material. In some embodiments, the handle is 3D printed using acrylonitrile butadiene styrene (ABS).

In some embodiments, design feature (ii) is addressed by utilizing brass collets that provide the frictional force necessary to prevent radial and axial displacement with respect to the handle assembly. Collets fabricated from other non-ferrous metals are also optionally used, such as those made from aluminum, titanium, and the like. In certain of these embodiments, these collets are clamped down by a 3D-printed wingnut onto a custom made collet adapter. The wingnut provides the ability to assemble and disassemble the elongated probe and sheath without the use of a wrench. Additionally, the collet adapters are constrained radially and axially in the handle assembly by using a cavity. These exemplary details are schematically depicted in a cross-section view of the assembly in FIG. 10.

In certain embodiments, design feature (iii) is addressed using a custom-designed actuation nut that produces linear retraction from corresponding rotary motion of the threaded knob as shown in FIG. 10. In these embodiments, the actuation nut functions similar to a lead screw mechanism used, for example, on milling machines, where axial loads on a milling table do not result in a change in linear displacement. With the elongated probe and sheath constrained by the brass collets, the Nitinol tendon is guided through the sheath from the elongated probe tip, then through the recess in the actuator assembly and attached to the knob via a knot. Consequently, linear displacement in the tendon results in deflection of the stylet tip. The exemplary knob and actuation nut shown in FIG. 10 do not have the threads modeled, but rather the dimensions of the knob rod and nut hole are such that a ¼-20 inch tap and die could be used, for example, to machine the threads. The tendon is typically preloaded by loosening the stylet wingnut, and then pressed on the back end of the elongated probe until the tip and tendon look qualitatively straight. The wingnut is then typically tightened again and the actuator knob can then be used to deflect the elongated probe is this embodiment.

An additional consideration is the extruded tendon guide that is included with the handle in this embodiment as shown in FIG. 10. The tendon guide is generally used to prevent excess loading on the sheath as the tendon tension is increased. Without the guide, a stress concentration at the exit of the sheath where the tendon rests may occur, causing excessive bending inside the handle as the tendon tension increased, potentially resulting in a failure mode.

In other embodiments, a single piece design of the tissue analysis device (e.g., virtual biopsy gun) is used, which does not include, for example, a separate distal stylet and a more proximal concentric metallic sheath. As shown in the exemplary embodiment depicted in FIG. 11 (panels A and B), a single, 300 mm long, 1.4 mm diameter proximal thick-walled (e.g., 0.3 mm wall) metallic tube 1101 is soldered or otherwise attached to a thin-walled (e.g., 0.1 mm wall) metallic tube 1103 (e.g., 1 mm in diameter, 20 mm in length), which is utilized for deflection, since it is typically more complaint than the thick-walled metallic tube. Furthermore, this compliant piece is generally soldered to the most distal solid piece of round stock 1105 (e.g., 1.4 mm in diameter, 30 mm in length). In these embodiments, the RF tracking coils 1107 are placed in grooves machined into the solid piece of round stock as shown. The RF imaging coils 1109 are placed radially in grooves disposed in the exterior of the most proximal thick-walled metallic tube (e.g., 1.4 mm diameter), at a location proximal to the region utilized for deflection. The actuating tendon is soldered or otherwise attached to the distal end of the thin tube, and runs entirely within the tubes in these exemplary embodiments. When tendon retraction occurs, the thin-walled tube deflects the entire distal end of the elongated probe.

Figure 16:
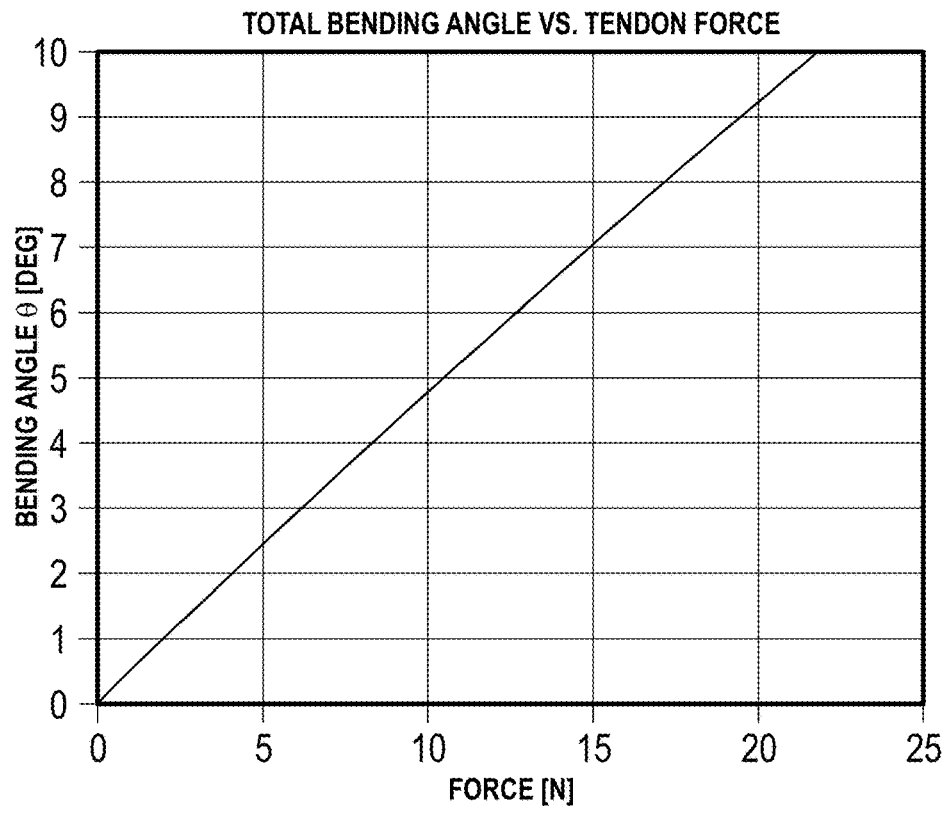
FIG. 16 is a plot of total bending or deflection angle (y-axis (θ [degrees])) versus tendon force (x-axis (Newton (N))) according to one device deflection modeling embodiment.
Figure 17:
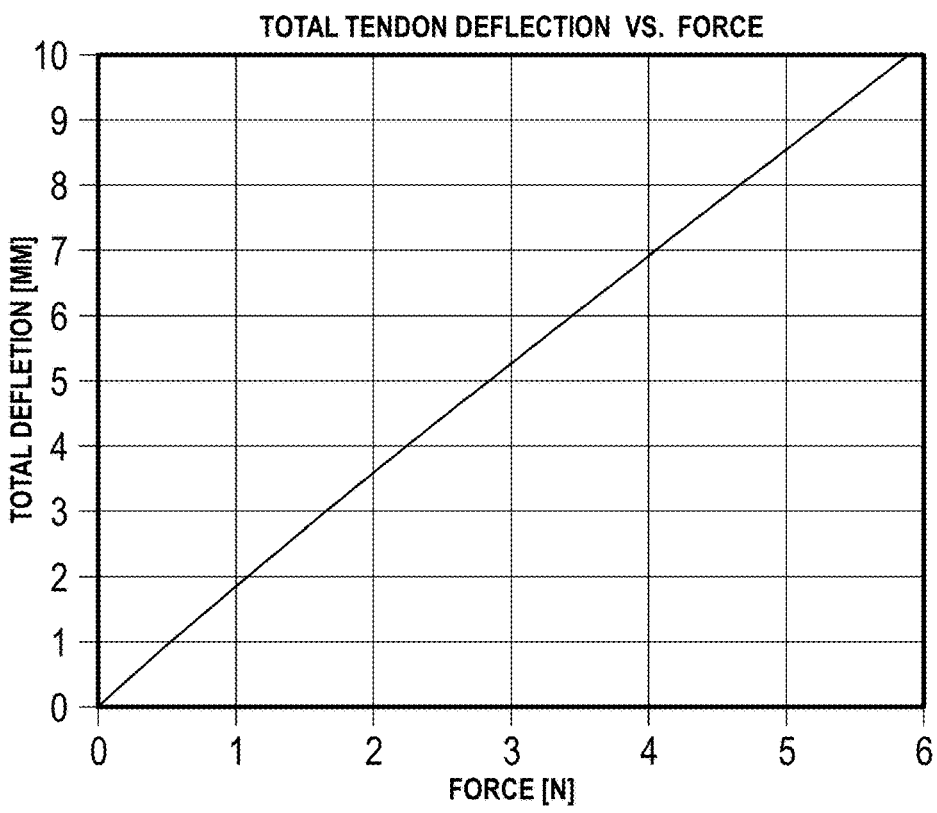
FIG. 17 is a plot of total tendon deflection or displacement distance (y-axis (mm])) versus tendon force (x-axis (Newton (N))) according to one device deflection modeling embodiment.

To further illustrate, FIGS. 12-15 schematically show an elongated probe from various views according to one exemplary embodiment. As shown, elongated probe 1200 (shown as including deflectable tube 1213) includes cavity 1215 in which co-axial cables 1211 and tendon 1205 are at least partially disposed. Cavity 1215 is disposed substantially through a length of elongated probe 1200. Co-axial cables 1211 are operably connected to RF tracking elements 1207 and 1209, which are mounted on stylet 1201 of elongated probe 1200. As also shown, elongated probe 1200 also includes deflectable region 1203 that deflects when the deflection mechanism of the device deflects positioning of elongated probe 1200. Deflectable region 1203 includes an array of orifices (shown as indentations disposed substantially perpendicular to a longitudinal axis of elongated probe 1200) that is disposed partially through elongated probe 1200 and that communicates with cavity 1215. Deflectable regions (e.g., deflectable region 1203) and/or filled regions of elongated probes (e.g., elongated probe 1200) are typically used to modulate the flexibility or elastic properties of the elongated probes (e.g., by affecting the degree of deflection and/or shape of the probes). For example, an area in which a given deflectable tube is cut or otherwise includes indentations creates a more flexible region, which can act the central radius of deflection in certain embodiments. In other areas, a given deflectable tube is at least partially filled with a filler (e.g., a stiff metallic filler, etc.), which creates stiff regions that are less amenable to deflection than the deflection regions. When such a stiff region is located near a terminus of a deflectable tube, that region can be used to puncture tissue in some embodiments. Tendon 1205 is operably connected to an end of elongated probe 1200 that is insertable into tissue and is also operably connected to a tension adjustment element operably connected to the handle (not within view). Tension adjustment elements, handles, and other device components are described further herein. Exemplary deflection modeling of use with the devices disclosed herein is shown in FIGS. 16 and 17. In particular, FIG. 16 is a plot of total bending or deflection angle (y-axis (θ [degrees])) versus tendon force (x-axis (Newton (N))), while FIG. 17 is a plot of total tendon deflection or displacement distance (y-axis (mm])) versus tendon force (x-axis (Newton (N))) according to certain embodiments.

Figure 18:
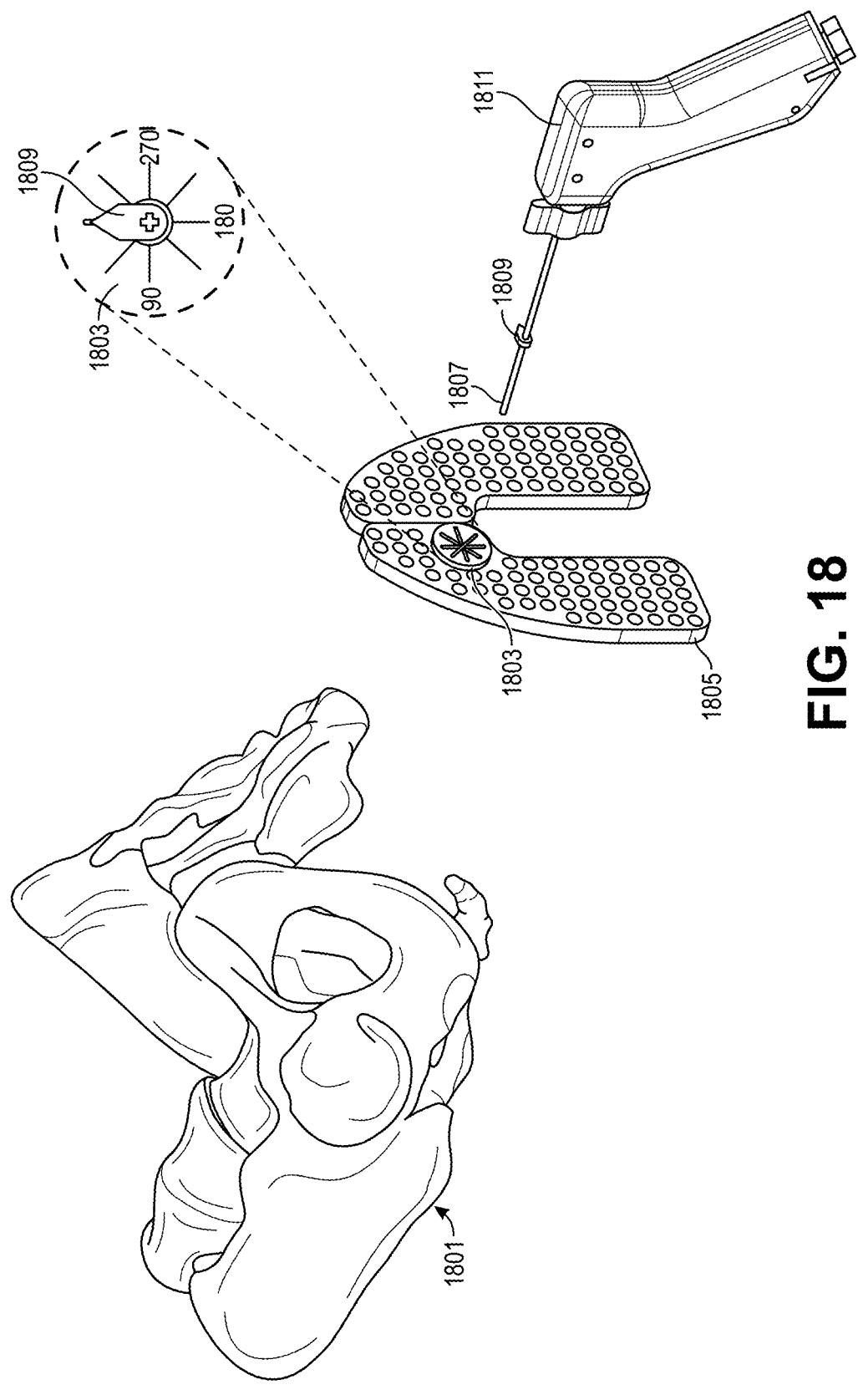
FIG. 18 schematically depicts components of an axial rotational control mechanism from a perspective view according to one exemplary embodiment.
Figure 19:
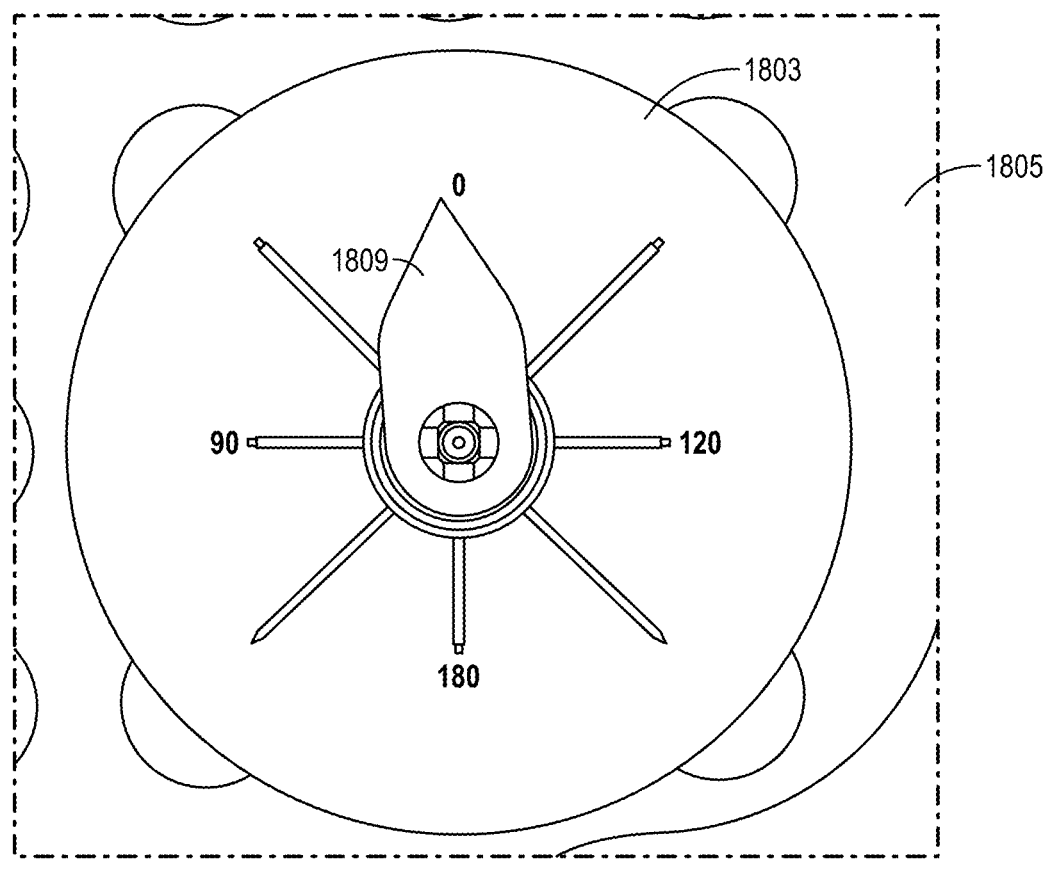
FIG. 19 schematically depicts the components of the axial rotational control mechanism from FIG. 18 from a front view.
Figure 20A:
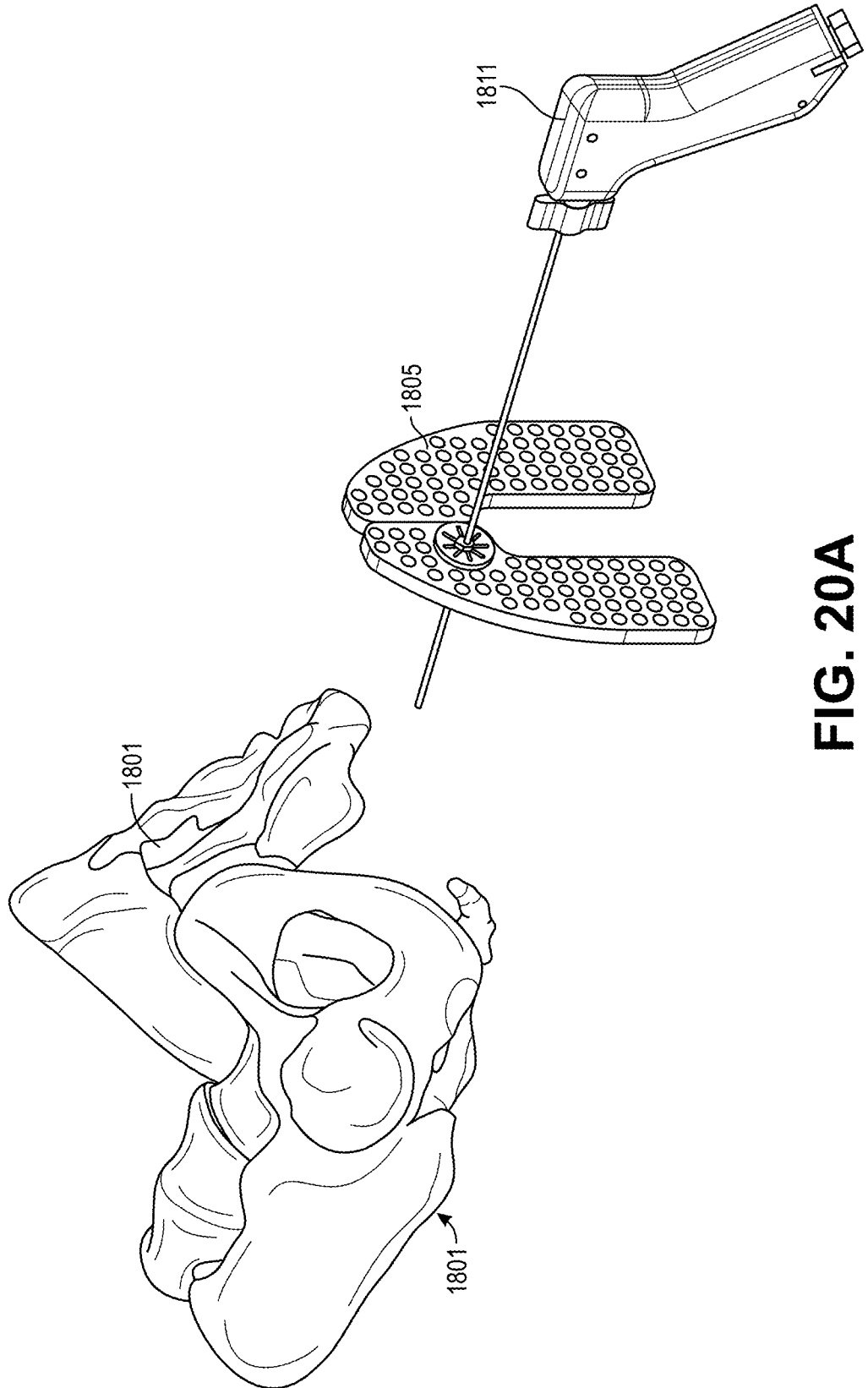
FIGS. 20A-G schematically depict the components of the axial rotational control mechanism from FIG. 18 from various perspective views.
Figure 20B:
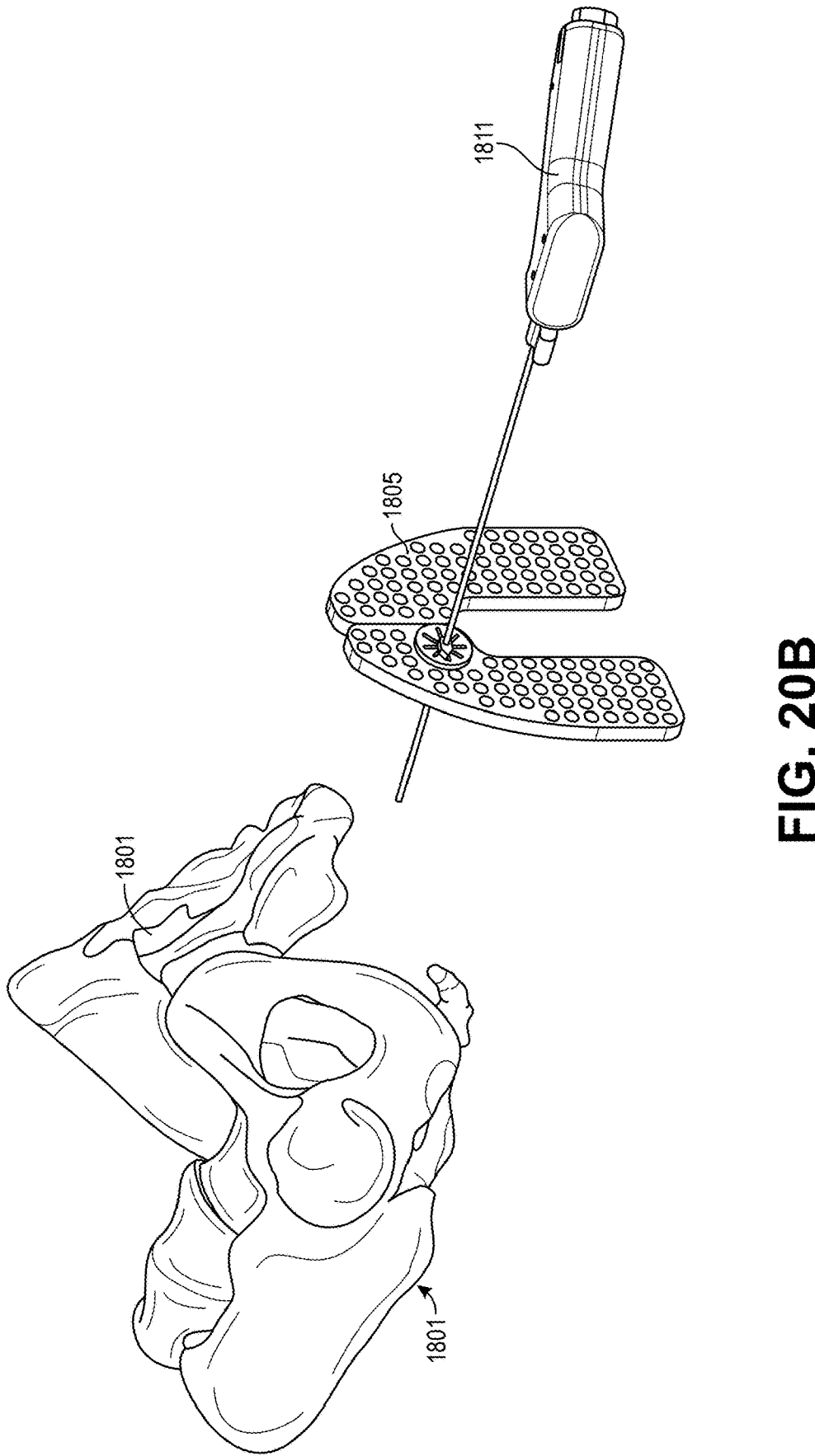
Figure 20C:
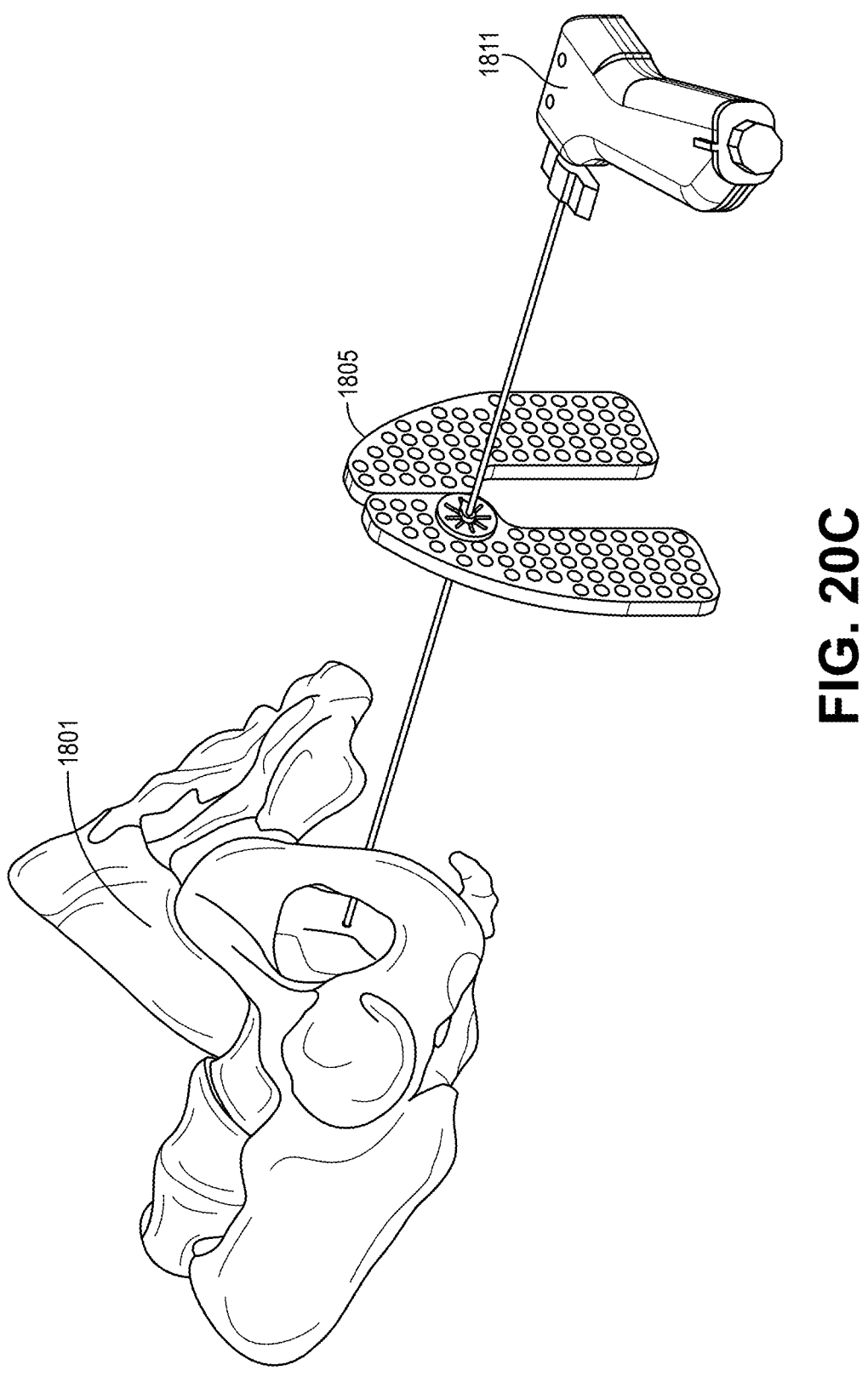
Figure 20D:
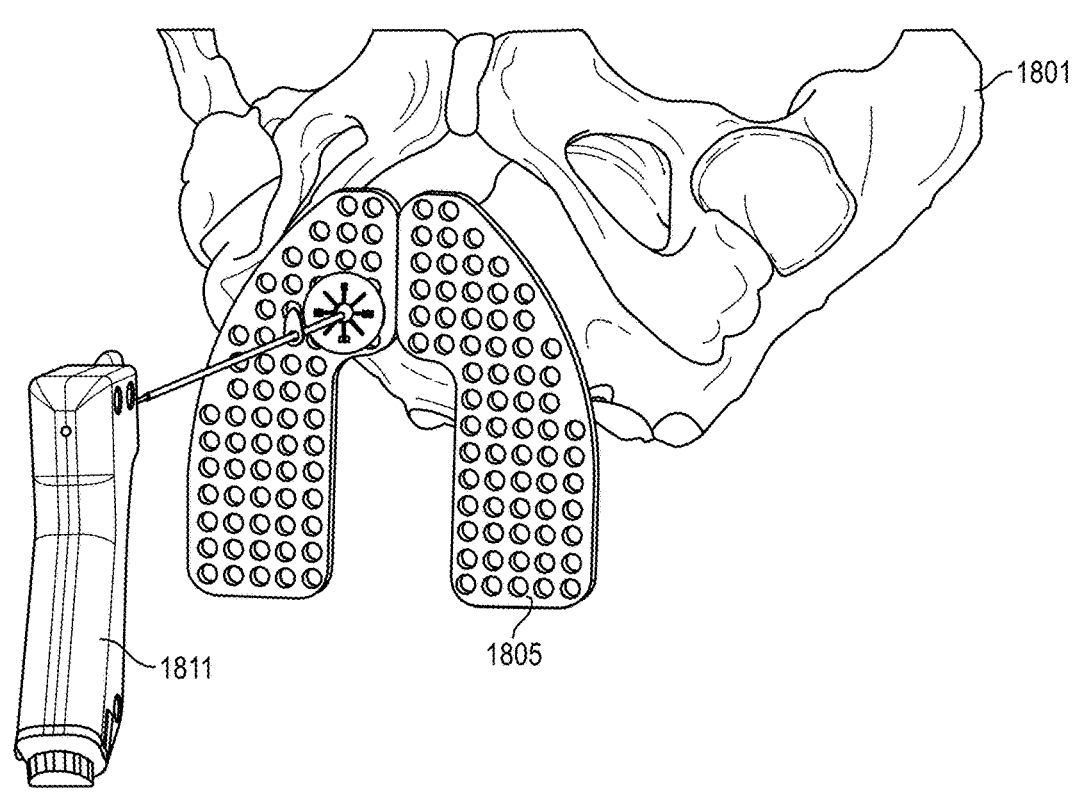
Figure 20E:
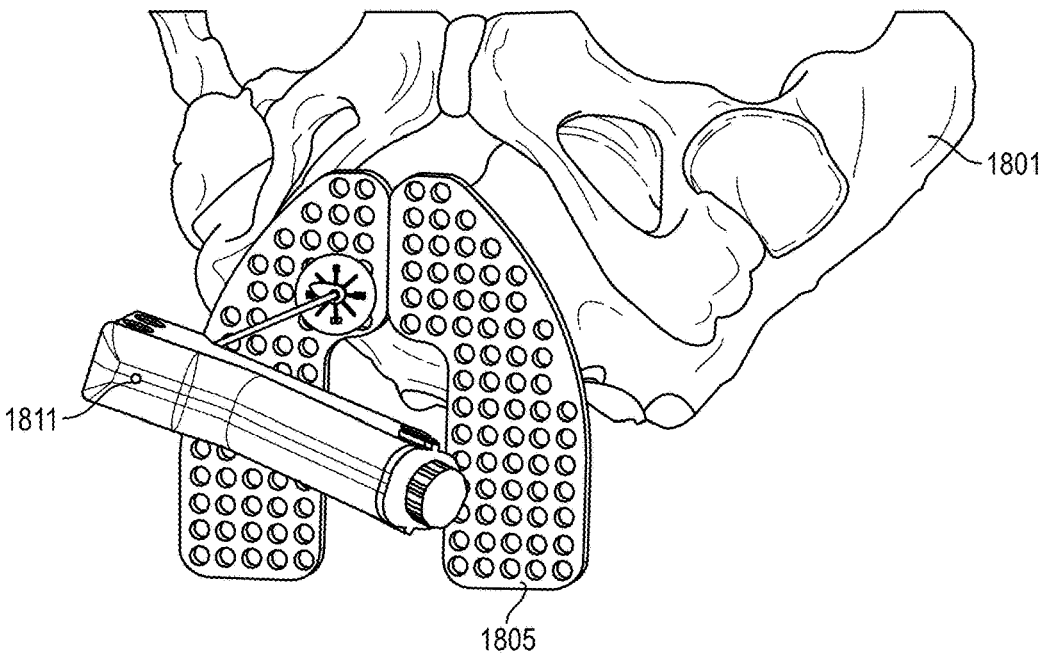
Figure 20F:
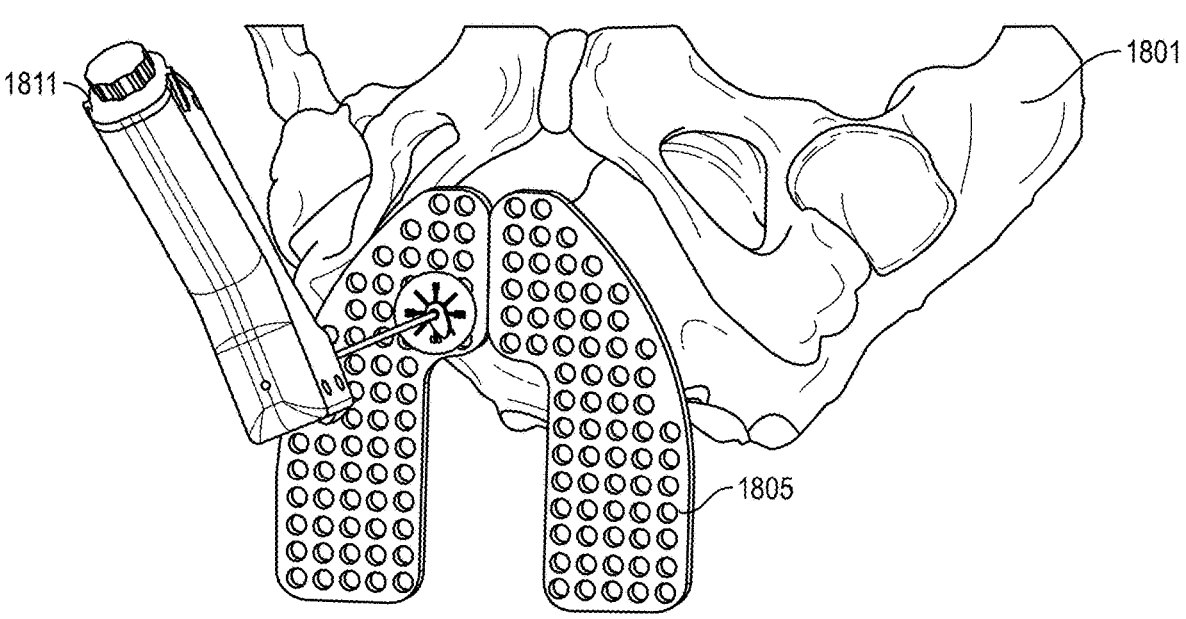
Figure 20G:
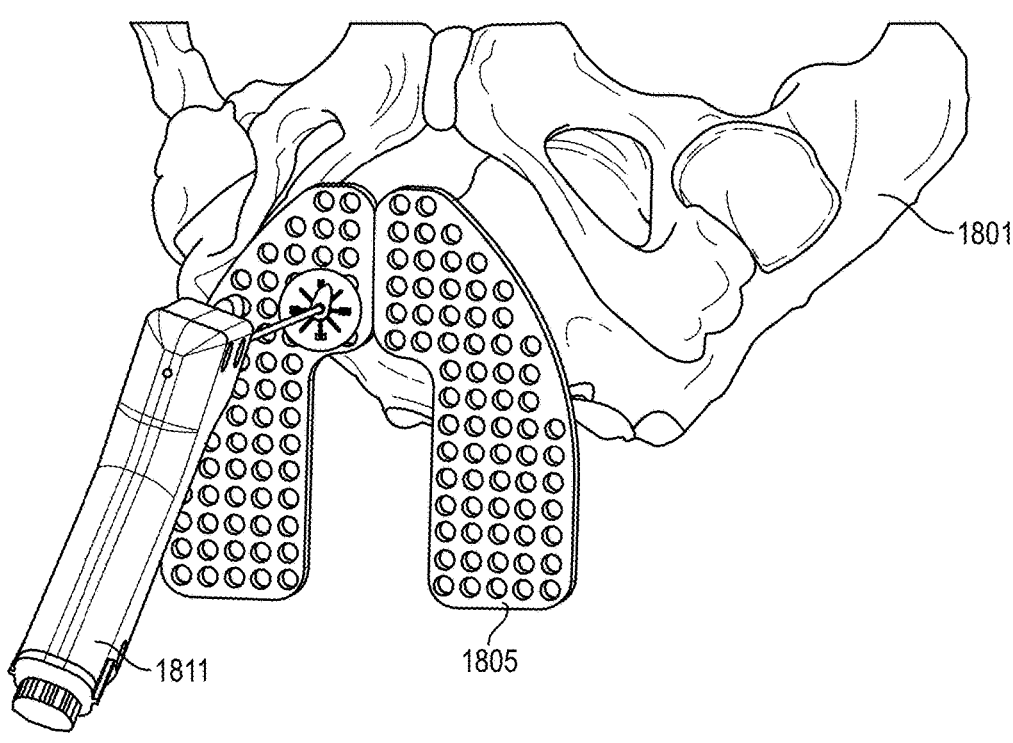

FIGS. 18-20 schematically depict components of an axial rotational control mechanism that can be used with the devices disclosed herein from various views according to one exemplary embodiment. As shown, the axial rotational control mechanism includes dial indicator 1809 operably connected to an elongated probe of device 1811 and dial 1803 operably connected to template device 1805 (e.g., a brachytherapy template or the like). Dial indicator 1809 indicates rotational angles formed between the elongated probe and template device 1805 (via angle indicator markings of dial 1803), for example, when the elongated probe is inserted into tissue (e.g., prostate tissue, cervical tissue, or the like) that is located proximal to pelvis 1801 of a given subject. In other words, steerable needle or elongated probe rotation angles can be determined from the difference between dial indicator 1809 and the angle indicator markings of dial 1803. During a given brachytherapy application, dial 1803 is typically operably connected (e.g., snap-locked) to template device 1805 at a selected position for therapy administration. In certain embodiments, dial indicator 1809 is removably positioned on (e.g., slid or clipped onto) the elongated probe of the device, whereas in other embodiments, dial indicator 1809 is fabricated integral with the elongated probe of the device. To further illustrate, FIGS. 20A-G schematically depict rotating device 1811 with dial indicator 1809 relative to dial 1803 attached to template device 1805 from various views.

Figure 21:
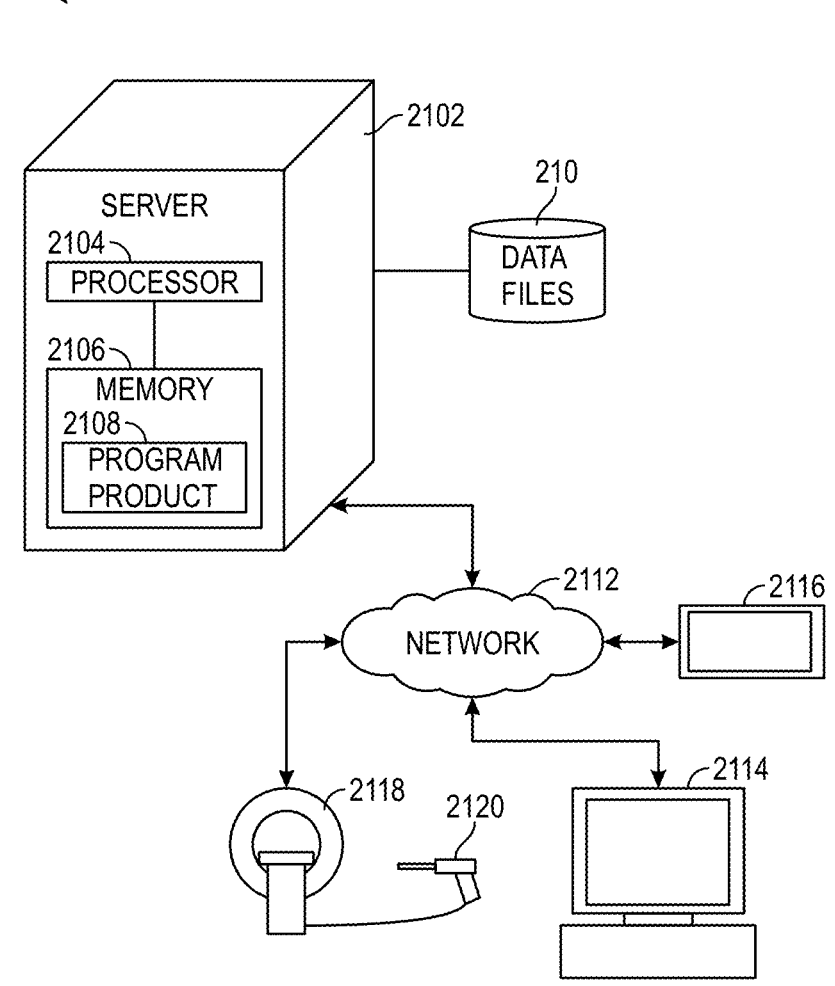
FIG. 21 is a schematic diagram of an exemplary system suitable for use with certain aspects disclosed herein.

The present disclosure also provides various systems and computer program products or machine readable media. In some aspects, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like. To illustrate, FIG. 21 provides a schematic diagram of an exemplary system suitable for use with implementing at least aspects of the methods disclosed in this application. As shown, system 2100 includes at least one controller or computer, e.g., server 2102 (e.g., a search engine server), which includes processor 2104 and memory, storage device, or memory component 2106, and one or more other communication devices 2114, 2116, (e.g., client-side computer terminals, telephones, tablets, laptops, other mobile devices, etc. (e.g., for receiving captured images for further analysis, etc.)) positioned remote from MRI apparatus 2118 and tissue analysis device 2120, and in communication with the remote server 2102, through electronic communication network 2112, such as the Internet or other internetwork. Communication devices 2114, 2116 typically include an electronic display (e.g., an internet enabled computer or the like) in communication with, e.g., server 2102 computer over network 2112 in which the electronic display comprises a user interface (e.g., a graphical user interface (GUI), a web-based user interface, and/or the like) for displaying results upon implementing the methods described herein. In certain aspects, communication networks also encompass the physical transfer of data from one location to another, for example, using a hard drive, thumb drive, or other data storage mechanism. System 2100 also includes program product 2108 stored on a computer or machine readable medium, such as, for example, one or more of various types of memory, such as memory 2106 of server 2102, that is readable by the server 2102, to facilitate, for example, a guided search application or other executable by one or more other communication devices, such as 2114 (schematically shown as a desktop or personal computer). In some aspects, system 2100 optionally also includes at least one database server, such as, for example, server 2110 associated with an online website having data stored thereon (e.g., entries corresponding to more reference images, indexed therapies, etc.) searchable either directly or through search engine server 2102. System 2100 optionally also includes one or more other servers positioned remotely from server 2102, each of which are optionally associated with one or more database servers 2110 located remotely or located local to each of the other servers. The other servers can beneficially provide service to geographically remote users and enhance geographically distributed operations.

As understood by those of ordinary skill in the art, memory 2106 of the server 2102 optionally includes volatile and/or nonvolatile memory including, for example, RAM, ROM, and magnetic or optical disks, among others. It is also understood by those of ordinary skill in the art that although illustrated as a single server, the illustrated configuration of server 2102 is given only by way of example and that other types of servers or computers configured according to various other methodologies or architectures can also be used. Server 2102 shown schematically in FIG. 21, represents a server or server cluster or server farm and is not limited to any individual physical server. The server site may be deployed as a server farm or server cluster managed by a server hosting provider. The number of servers and their architecture and configuration may be increased based on usage, demand and capacity requirements for the system 2100. As also understood by those of ordinary skill in the art, other user communication devices 2114, 2116 in these aspects, for example, can be a laptop, desktop, tablet, personal digital assistant (PDA), cell phone, server, or other types of computers. As known and understood by those of ordinary skill in the art, network 2112 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or machine readable medium 2108 is optionally in the form of microcode, programs, cloud computing format, routines, and/or symbolic languages that provide one or more sets of ordered operations that control the functioning of the hardware and direct its operation. Program product 2108, according to an exemplary aspect, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 2108 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 2108 is optionally copied from the computer-readable medium to a hard disk or a similar intermediate storage medium. When program product 2108, or portions thereof, are to be run, it is optionally loaded from their distribution medium, their intermediate storage medium, or the like into the execution memory of one or more computers, configuring the computer(s) to act in accordance with the functionality or method of various aspects. All such operations are well known to those of ordinary skill in the art of, for example, computer systems.

To further illustrate, in certain aspects, this application provides systems that include one or more processors, and one or more memory components in communication with the processor. The memory component typically includes one or more instructions that, when executed, cause the processor to provide information that causes at least one captured tissue images and/or the like to be displayed (e.g., via communication devices 2114, 2116 or the like) and/or receive information from other system components and/or from a system user (e.g., via communication devices 2114, 2116, or the like).

In some aspects, program product 2108 includes non-transitory computer-executable instructions which, when executed by electronic processor 2104 perform at least: tracking positions of an elongated probe of a magnetic resonance imaging (MRI) compatible tissue analysis device, as described herein, in substantially real-time when the elongated probe is inserted into a tissue (e.g., in-situ in a given subject), and capturing images of the elongated probe and/or the tissue in substantially real-time when the elongated probe is inserted into the tissue. Typically, the instructions perform at least one MRI pulse sequence.

System 2100 also typically includes additional system components (e.g., MRI apparatus 2118 and tissue analysis device 2120) that are configured to perform various aspects of the methods described herein. In some of these aspects, one or more of these additional system components are positioned remote from and in communication with the remote server 2102 through electronic communication network 2112, whereas in other aspects, one or more of these additional system components are positioned local, and in communication with server 2102 (i.e., in the absence of electronic communication network 2112) or directly with, for example, desktop computer 2114.

Figures 25, 26:
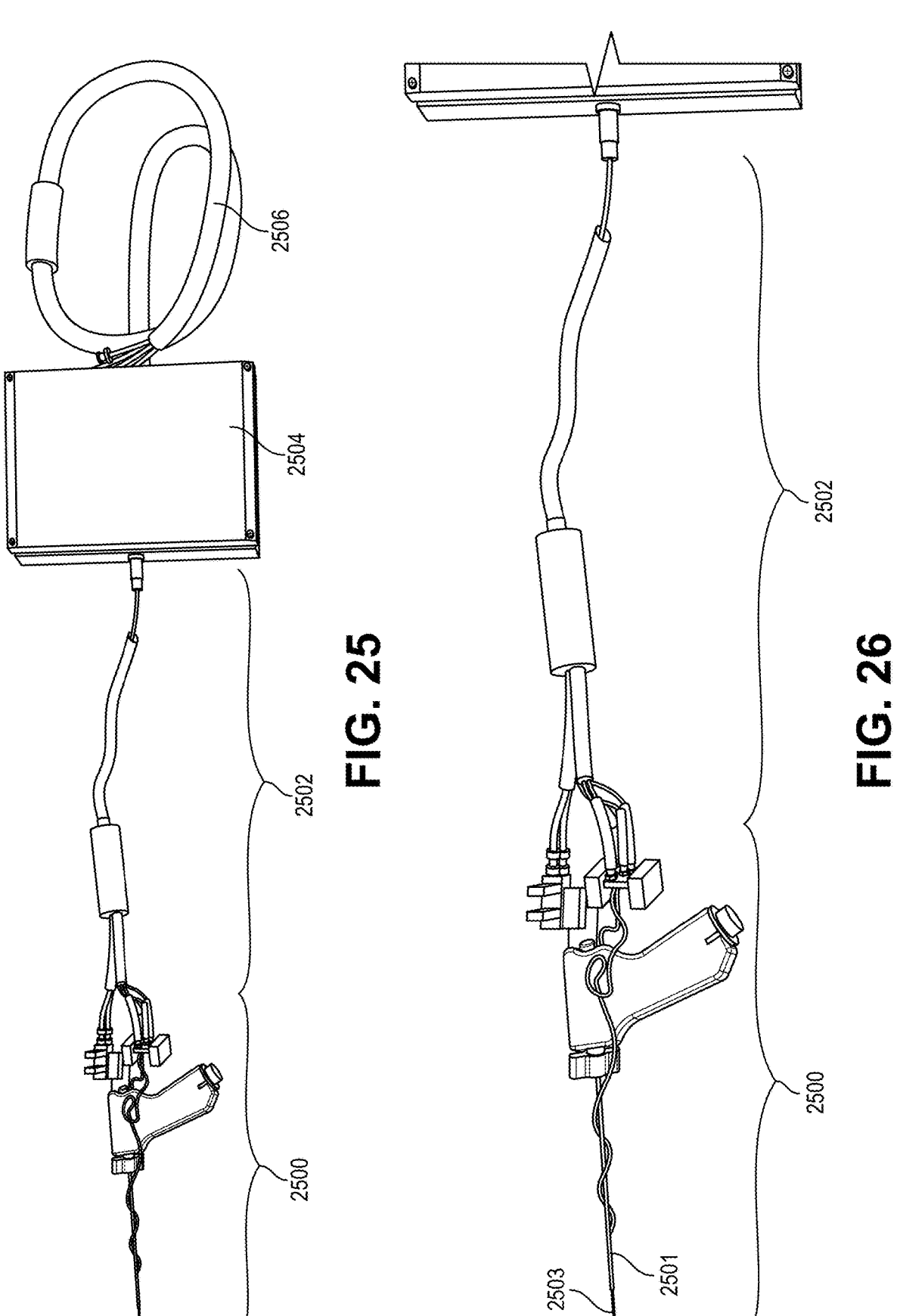
FIG. 25 is an image that shows a cable configuration for connecting an MRI compatible tissue analysis device to an MRI apparatus, which cable configuration includes a system box, according to one exemplary embodiment.
FIG. 26 is an image that shows a more detailed view of the MRI compatible tissue analysis device operably connected to a selectively connectable cable that includes a Balun from the image of FIG. 25.

In some embodiments, an MRI compatible tissue analysis device as described herein is connected to an MRI apparatus (e.g., tissue analysis device 2120 and MRI apparatus 2118) via a cable configuration that includes a system box or housing that houses electronics components. FIGS. 25-30 A and B show aspects of such a cable configuration according to one embodiment. FIGS. 25 and 26, for example, show images of a cable configuration, or components thereof, for connecting an MRI compatible tissue analysis device to an MRI apparatus, which cable configuration includes system box 2504, which includes a signal amplification mechanism (e.g., signal amplification circuit elements). As shown, RF tracking elements 2503 (e.g., two tracking coils) and RF imaging elements 2501 (e.g., four imaging coils) of tissue analysis device 2500 are operably connected to selectively connectable cable 2502 that is operably connected to system box 2504. In certain embodiments, tissue analysis device 2500 is used to conduct virtual biopsies along brachytherapy needle trajectories. In the embodiment shown, selectively connectable cable 2502 is a 1.5 T MRI-conditional quick-release cable connection that includes a Balun for heat amelioration. The quick-release cable connection allows for the rapid exchange of tissue analysis device 2500 from system box 2504 for another device. As also shown, system box 2504 also includes cables 2506, which are connectable to an MRI apparatus or receiver. In the embodiment shown, cables 2506 are 1.5 T (i.e. 63.8 MHz) MRI-conditional half-wavelength length cables that also include resonant RF traps (i.e., Baluns) for heat amelioration.

Figure 27:
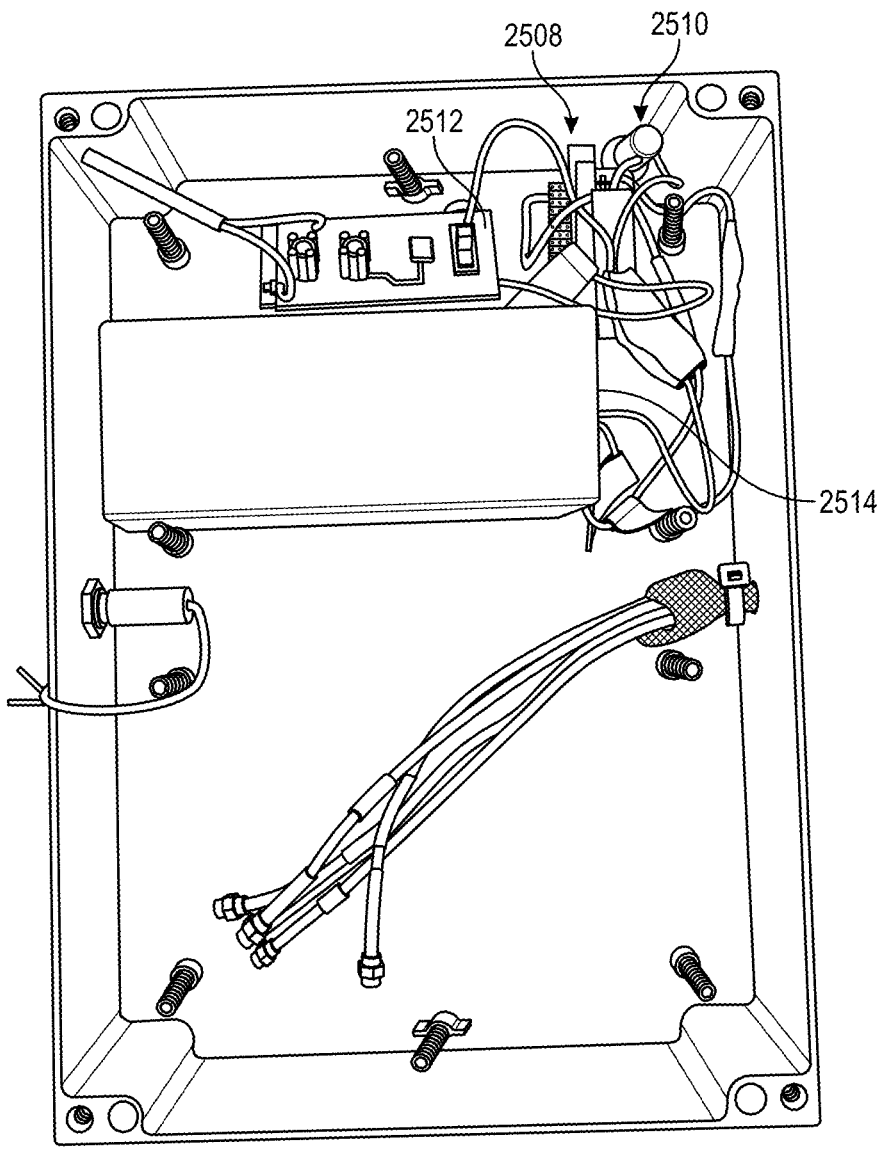
FIG. 27 is an image that shows a bottom layer of the system box from the image of FIG. 25.
Figure 28:
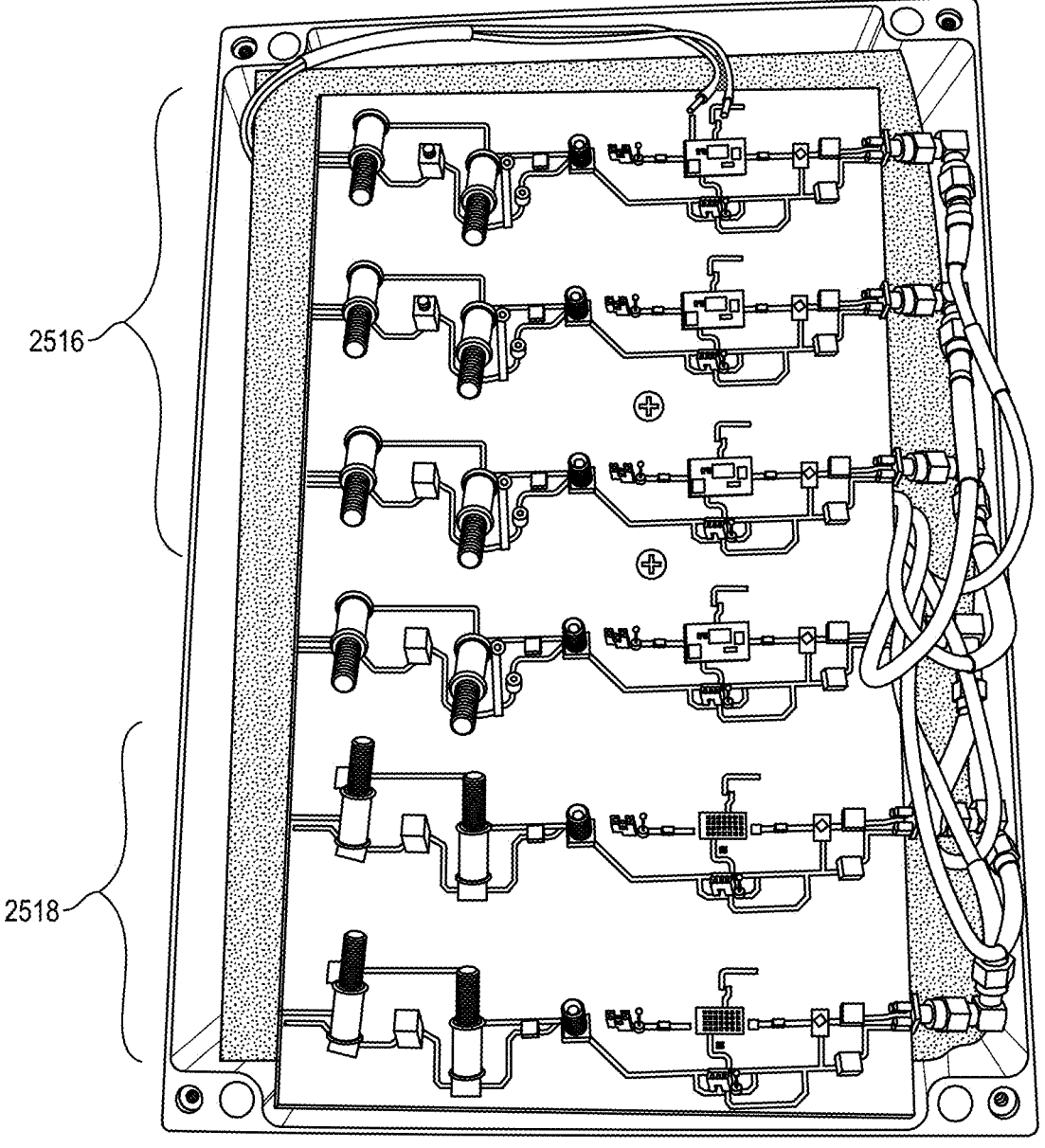
FIG. 28 is an image that shows a top layer of the system box from the image of FIG. 25.
Figure 29:
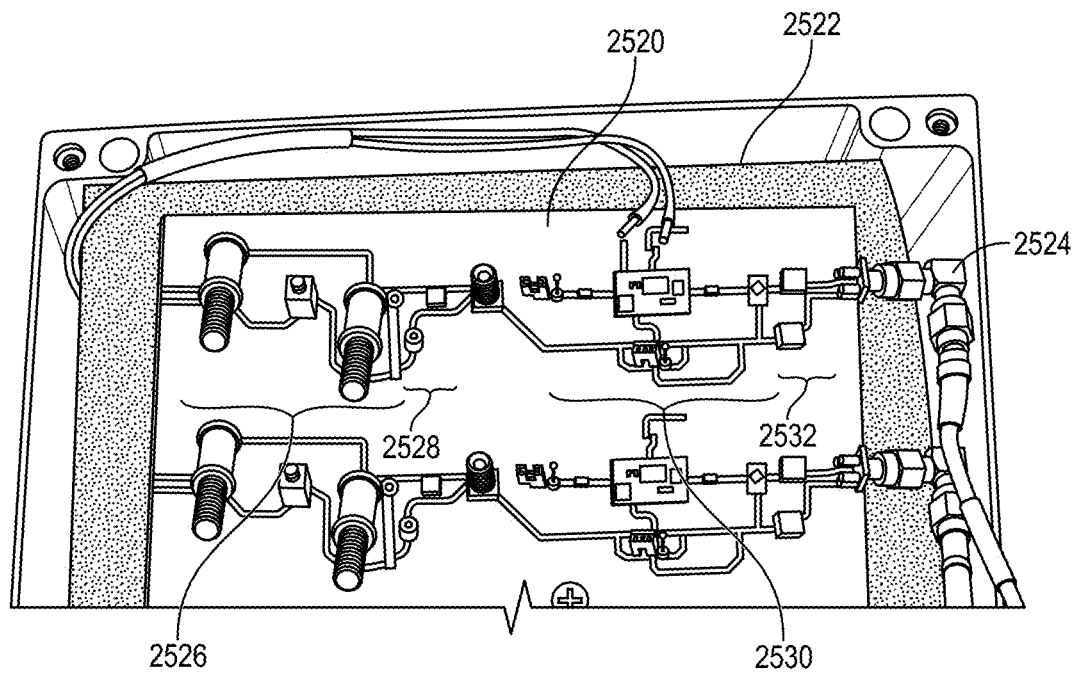
FIG. 29 is an image that shows an imaging channel of the system box from the image of FIG. 25.
Figure 30A:
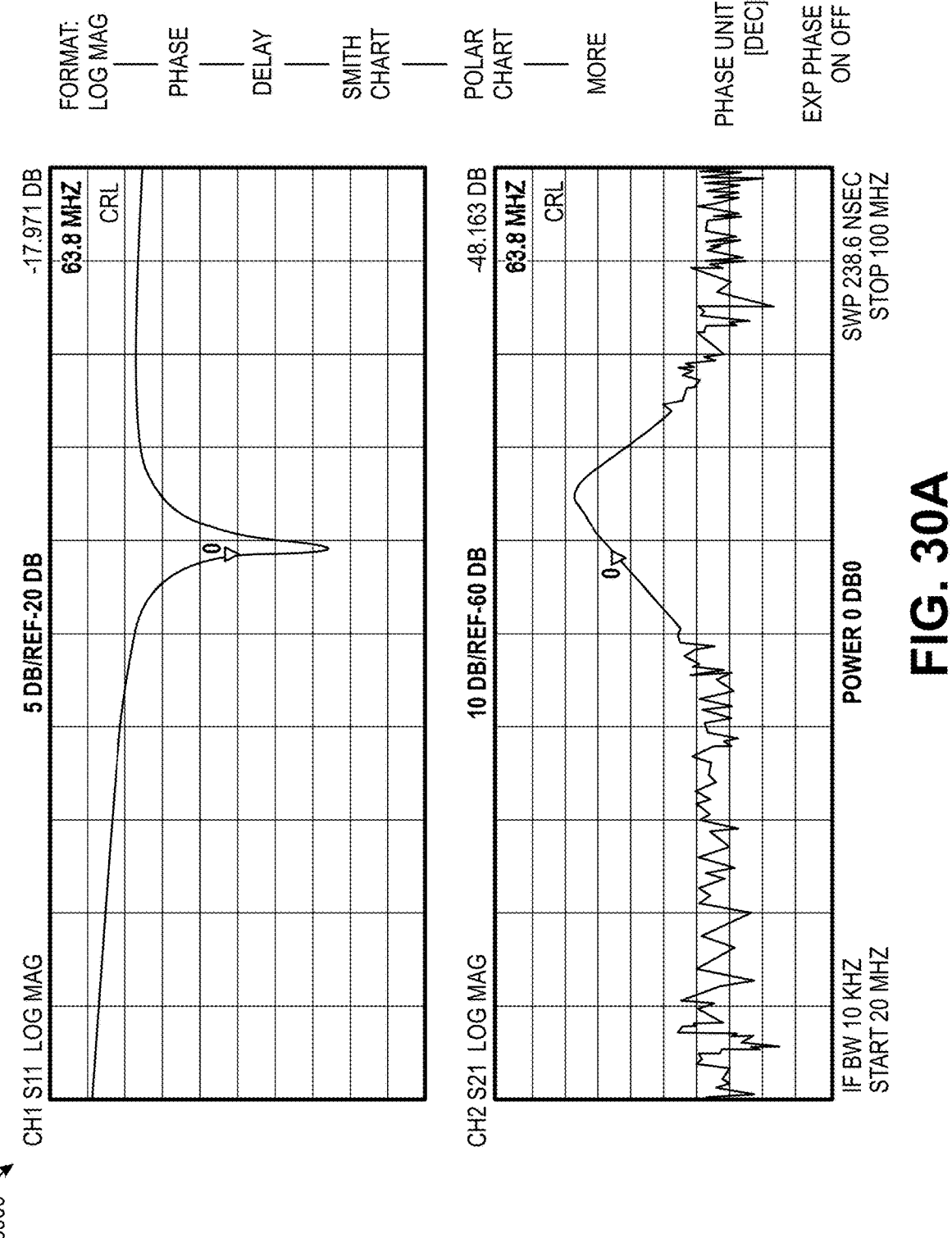
FIGS. 30A and B are images that show Vector Network Analyzer plots of a low noise amplification of an imaging signal before and after gain, respectively, according to one exemplary embodiment.
Figure 30B:
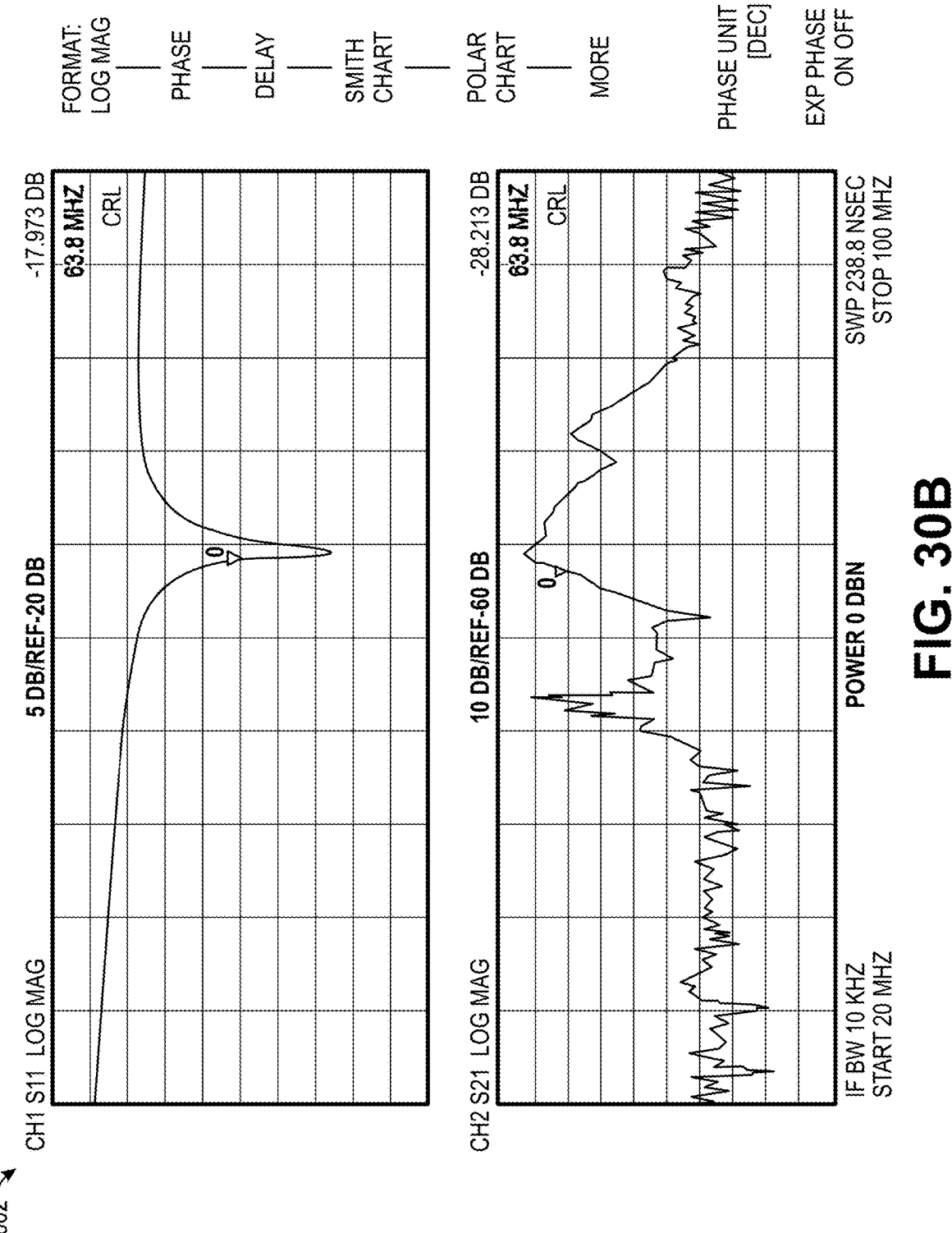

System box 2504 houses various electronics components, including tuning, matching, decoupling, signal amplification/variable gain, patient isolation, imaging channel, and tracking channel circuit elements. In the embodiment shown, system box 2504 includes dedicated tuning, matching and decoupling circuits, and primarily low noise pre-amplifiers (LNAs) placed very close to the tissue analysis device (i.e., between patients and the MRI receiver) to insure capturing maximal signal-to-noise (SNR) from the imaging coils. More specifically, FIG. 27 is an image that shows a bottom layer of the system box 2504. As shown, the bottom layer includes on-off switch 2508, battery charger 2510, an MR-conditional bias-T circuit 2512, and an MR-conditional lithium polymer battery 2514 (e.g., an 18-V Powerstream MR-conditional lithium polymer battery). MR-conditional bias-T 2512 prevents RF interference from battery 2514 and RF to battery 2514, and in certain embodiments, includes one parallel 0.1 µF capacitor, two series Coilcraft 1.5 µH air-core inductors, and a 10 Ohm series resistor. FIG. 28 is an image that shows a top layer of system box 2504, which includes imaging channels 2516 (1-4) and tracking channels 2518 (1-2). FIG. 29 is an image that shows an imaging channel of the system box 2504. As shown, the imaging channel includes tuning and matching circuit elements 2526 (shown as a π circuit with Knowles AJ40HV tunable capacitors and Coilcraft 164-11A06L variable inductors), decoupling (crossed) diodes 2528 (Macom MADP-011048-TR3000), variable gain circuit 2530 (pre-amplification and attenuator), port 2520 to measure signal before gain, port 2524 to measure signal after gain (connect to an MRI apparatus or receiver), patient isolation circuit element 2532, and power source 2522 (11V DC power source). Variable gain circuit 2530 allows for attenuating signal to conform to surface coil intensity. In the embodiment shown, variable gain circuit 2530 includes a tuned (63.8 MHz) amplifier (Wantcom WMA1R5A) and an attenuator (Minicrafts GAT-10+ to GAT-20+). FIGS. 30 A and B are images that shows plots of a low noise amplification of an imaging signal before (−48 dB at 63.8 MHz) 3000 and after (−28 dB at 63.8 MHz) 3002 gain, respectively, which represents approximately a 20 dB gain (28 dB amplifier followed by 10 dB attenuator). In addition, in the embodiment shown, patient isolation circuit element 2532 (shown as a Kemet 0.1 µF C2220x104KDRAACAUTO) does not pass DC<3 KV or 60 Hz current >10 µA, which is required according to ASTM/IEC requirements in order to meet electrical requirements from interventional medical devices.

Additional details relating to computer systems and networks, databases, and computer program products are also provided in, for example, Peterson, *Computer Networks: A Systems Approach*, Morgan Kaufmann, 5th Ed. (2011), Kurose, *Computer Networking: A Top-Down Approach*, Pearson, 7*th* Ed. (2016), Elmasri, *Fundamentals of Database Systems*, Addison Wesley, 6th Ed. (2010), Coronel, *Database Systems: Design, Implementation, & Management*, Cengage Learning, 11*th* Ed. (2014), Tucker, *Programming Languages*, McGraw-Hill Science/Engineering/Math, 2nd Ed. (2006), and Rhoton, *Cloud Computing Architected: Solution Design Handbook*, Recursive Press (2011), which are each incorporated by reference in their entirety.

EXAMPLE 1

Figure 22B:
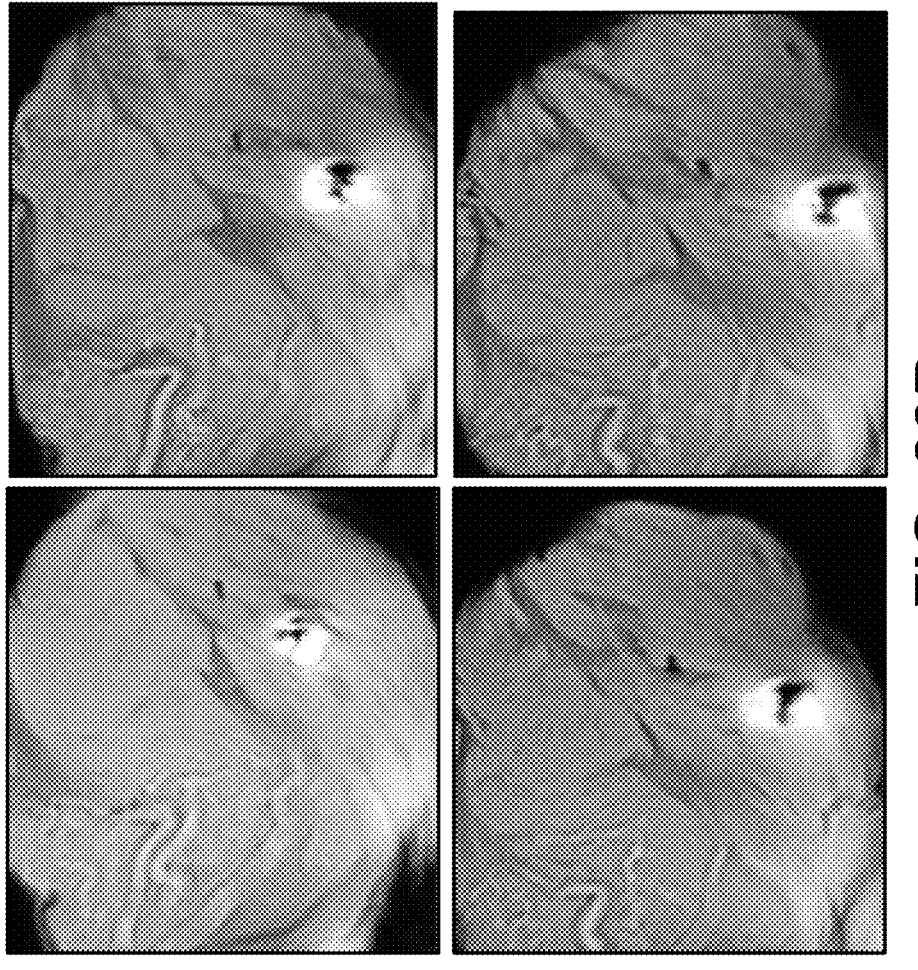
FIG. 22 show UTE images of an elongated probe inside tissue. Panel A shows a sensitivity region of the imaging array, while Panel B shows zoomed stack of spirals Inversion-Recovery Ultra Short Time-to-Echo 0.9×0.9×1.8 mm³, 2:24 minutes/48 slices.
Figure 22A:
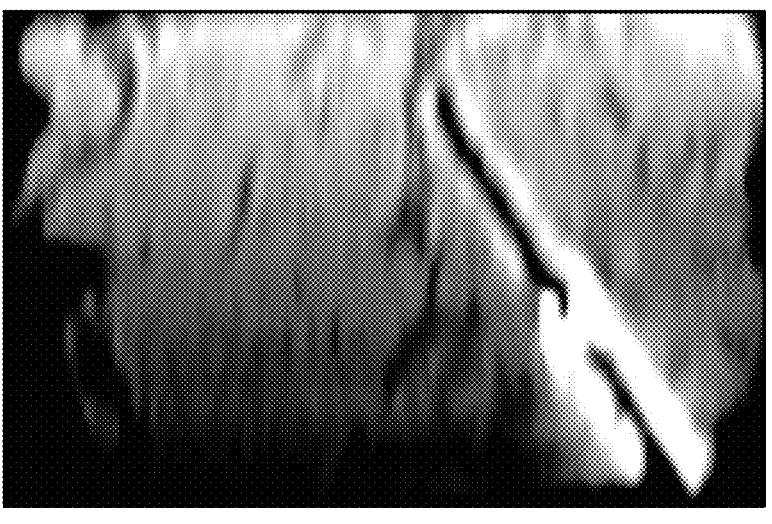

A deflectable high-resolution theranostics system that carries the MRI tracking and imaging micro coils as described herein was evaluated for tissue characterization. The device was successful at deflecting the elongated probe (stylet) tip up to an angle of approximately 45° with respect to the longitudinal axis of the sheath. Additionally, the knob was able to be tightened and the elongated probe maintained its new position (see, e.g., the elongated probe deflection shown in FIG. 6). The system was tested in ex-vivo muscular bovine tissue, where the MR tracking coils detected path changes in the bovine sample of 45° in tip trajectory at a penetration depth of 120 mm. The device was MRI-safe within a 1.5-T scanner. Exemplary images are shown in FIG. 22.

Imaging was performed with the 4-channel array in a 30 cm field-of-view (FOV) saline phantom. The 4-channel array provided a signal-to-noise ratio (SNR) enhancement of 8-9× and 7-8×, at distances of 6 mm and 8 mm, respectively, from the tube surface relative to the spine array. The effective field of view was $30\times14\times14$ mm$^3$, which is significantly larger than possible with conventional OCT and IVUS methods.

EXAMPLE 2

Introduction

High-Dose-Rate brachytherapy of cervical cancer is performed after external beam radiation (EBRT), aiming to kill residual tumor-cells that survived EBRT by providing more-focused higher-dose radiation (HDR). Procedures commonly require implantation of 10-20 "needles" into residual-tumor regions. It is important to (I) determine exactly where the residual tumors are, and (II) deliver the correct radiation to them, since surviving cells may survive some level of radiation dose, while excessive dose may harm neighboring tissues. HDR brachytherapy treatments ("fractions") are commonly delivered each 6 hours over a 48-hour period.

Previously, non-invasive (e.g. surface-coil based) MRI imaging is widely performed prior to cervical-cancer brachytherapy-needle placement (Straub et al., "Radiation-induced fibrosis: mechanisms and implications for therapy," Cancer Res Clin Oncol, 141:1985-1994 (2015)), and MR-Tracked (MRT) active-needle placement is performed at two hospitals (Pohlers et al., "TGF-β and fibrosis in different organs—molecular pathway imprints," Biochimica et Biophysica Acta 1792:746-756 (2009)), at ~15-minute procedure speeds that rival ULS-guided needle placement (Messroghli et al., "Modified Look-Locker inversion recovery (MOLLI) for high-resolution $T_1$ mapping of the heart," Magn Reson Med 52:141-146 (2004)).

The devices and related aspects disclosed herein will foster an increased MR utilization, where (i) combined MRT and high-speed MRI, in tissues surrounding the punctures, are performed during needle placement in order to determine more precisely, along the needle's trajectory, where residual tumor or, alternatively, fibrotic tissue and post-radiation inflammation exists, as well as the degree of tissue hypoxia, which gages the dose requirements, and (ii) similar procedures are be performed between fractions to determine if therapy should be altered.

Extended MRI use involves (a) fast MRI procedures, so as not to excessively extend the procedures, and (b) high Contrast-to-Noise-Ratio per unit time (CNR/t) imaging of the desired tissue attributes. The present disclosure provides (a, b) by using miniature MRI arrays that can be brought very close to the tissues of interest using the same holes made for radiation-seed implantation, while penetrating into the tissues to a depth which extends beyond the highly-disturbed (torn) tissue layers that immediately surround the puncture hole. Exemplary MRI contrasts: Hypoxia measured with T2*(Kim et al., "Relationship of MRI delayed contrast enhancement to irreversible injury, infarct age, and contractile function," Circulation 100:1992-2002 (1999)), fibrosis with Short Inversion time-Ultrashort-TE (Caravan et al., "Collagen-Targeted MRI Contrast Agent for Molecular Imaging of Fibrosis," Angewandte Chemie 119:8319-8321 (2007)), and tissue metabolism with multiple-delay-time Contrast-Enhanced 3DGRE (de Jong, "Direct detection of myocardial fibrosis by MRI," *J. Mol. Cell. Cardiol.*, 51:974-979 (2011)).

Methods

Virtual Biopsy "Gun"

Figure 23A:
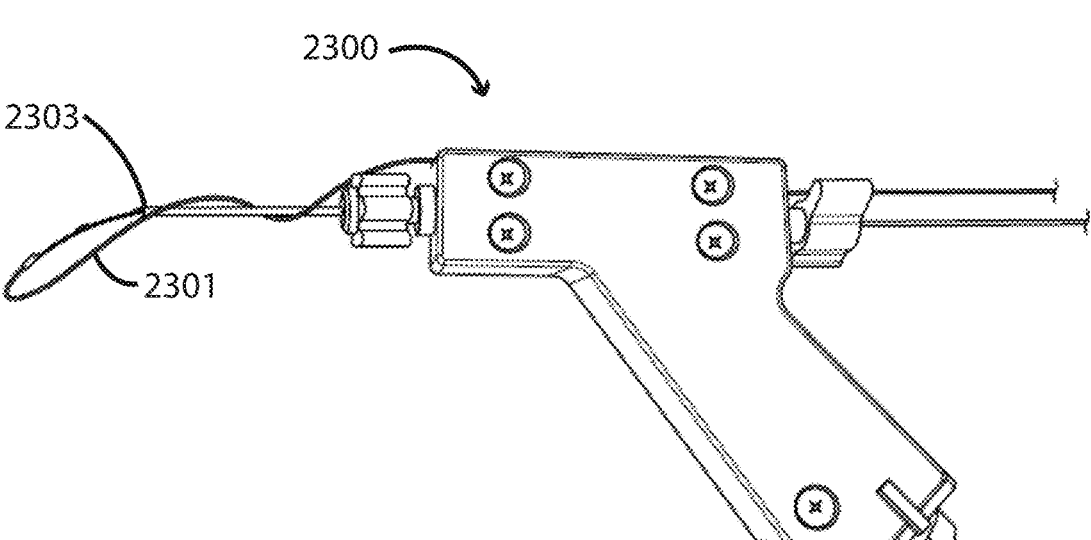
FIG. 23 (Panels A, B) are images of a deflectable virtual biopsy "gun" 2300 in deflected and straight orientations, respectively, from side views according to one embodiment. A pull-wire or tendon 2301 is used to deflect the elongated probe (stylet) tip 2303 of the gun. The tip is made of a pointed nitinol rod (the stylet) with dedicated groves for 2 MRT micro-coils, which localize the instantaneous tip location and orientation. The stylet serves to puncture tissues, creating hole trajectories which are, for example, used for inserting radiation seeds into tumors and their surroundings in certain applications. 10 mm behind and surrounding the stylet, is a nitinol tube or sheath, on which a miniature imaging array is mounted. The imaging array is used to image the walls of the puncture.
Figure 23B:
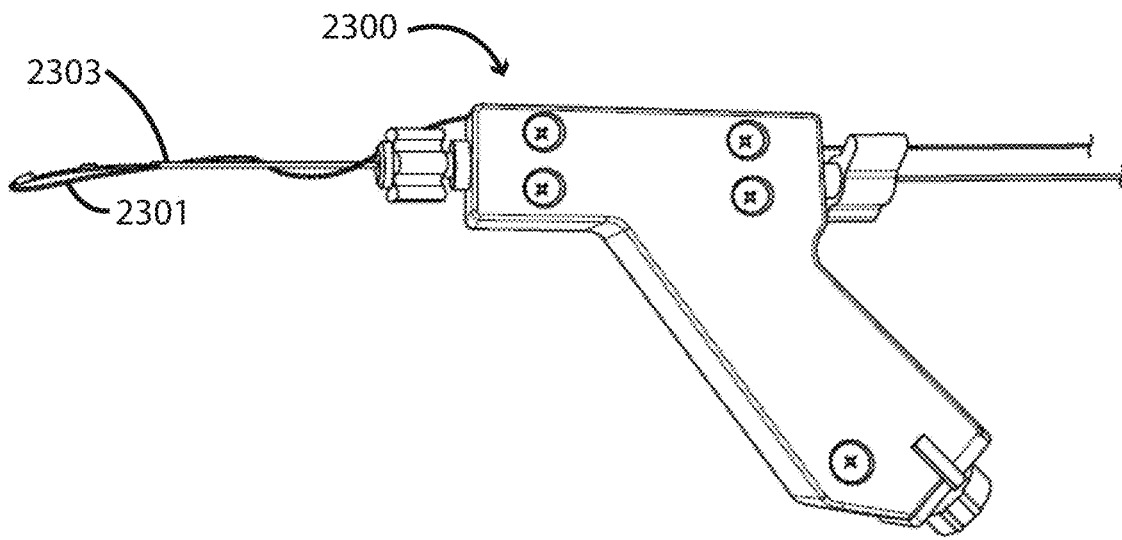
Figures 24A, 24B, 24C, 24D:
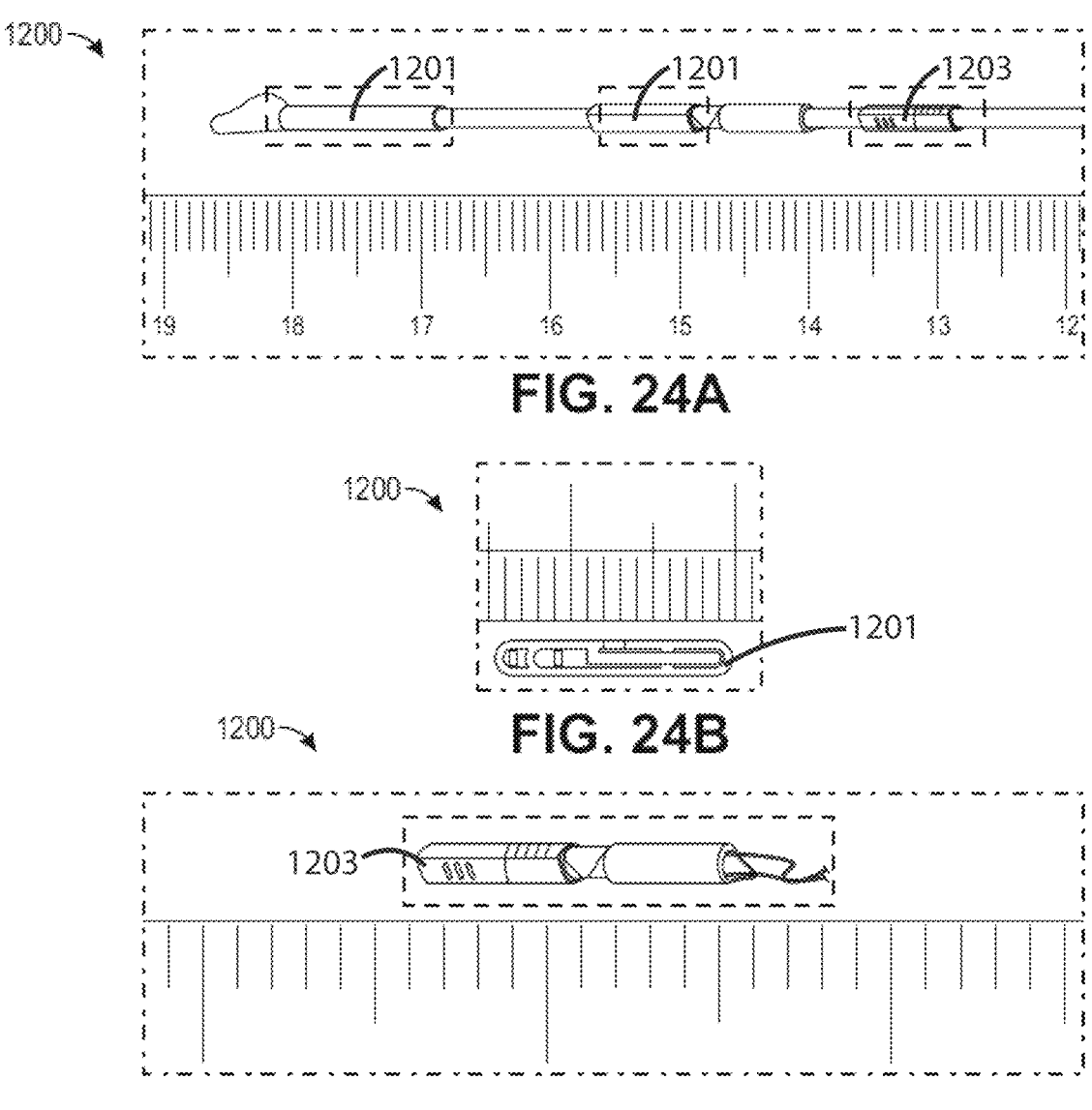
FIG. 24 (Panels A, B, C, D) are enlarged images of the distal region of the virtual biopsy gun 1200 from FIG. 12. Panel A includes two MRT coils 1201 on the deflectable distal stylet tip, and behind them the 4-channel imaging array 1203, which is mounted on the concentric tube. Panel B is a larger view image of the flexible printed circuit (FPC) 3-layer MRT coil. Panel C shows a larger view of the 4-channel MR imaging array, as mounted around the tube or sheath circumference and Panel D is a detailed view of an individual FPC miniature imaging coil. The 200-micron thick FPC coils employ embedded (parallel) tuning and (series) matching thin-film capacitors for enhanced signal-to-noise-ratio.

A (1.4 mm outer-diameter (OD), 330 mm length) flexible nitinol elongated probe (stylet), developed for MR-guided brachytherapy, was instrumented with a nitinol pull-wire. The tip location/orientation was provided at $0.8\times0.8\times0.8$ mm$^3$ resolution and 15 frames-per-second rate, using two MR-Tracking microcoils (3-layer flexible-printed-circuit (FPC) antennas Length:Width:Thickness=8 mm:1.1 mm:0.2 mm with embedded capacitors providing 63.8 MHz tuning and matching) placed in grooves along the elongated probe. A 2.1 mm OD nitinol tube was positioned with its distal end 10 mm behind the proximal MRT coil and mounted with a 4-coil array of tuned and matched miniature (2 layer FPC antennas, Length:Width:Thickness=14 mm:1.8 mm:0.2 mm) MR imaging coils, arranged at 90-degree increments on the tube circumference. A 0.3 mm thick mylar layer between the coils and the nitinol-tube served to increase their outward RF-lobe projection, employing the imagemagnetic-field concept. Signals from the tracking and imaging coils was transmitted up the elongated probe on 44 AWG micro-coaxial cable. Tip deflection (up to ~45 degrees) was activated by a rotary lever at the device or gun's base, which controlled pull-wire tension. The gun could thereby control the stylet's and imaging-array's penetration depth into the body, as well as the puncture direction, returning the trajectory back to the clinician's desired path by correcting for needle deflections resulting from the pelvic tissue's muscular composition. FIGS. 23 and 24 show images of the device or biopsy "gun" or components thereof used in this Example.

Mechanical Deflection

Ex-vivo muscular bovine tissue was tested. The degree of path deflection possible during perforation of the bovine sample was tested, with simultaneous MRT tracking of the changes enabling quantification of the actual deflection angles during maximum pull-wire tension.

Imaging

Phantom Imaging: Initial imaging was performed with the 4-channel array in a saline phantom, in order to compare the array's SNR with that of the commercial 1.5 T Siemens Aera scanner's spine arrays.

Ex-vivo Imaging: Performed in bovine shoulder tissue. Stacks of-Spirals UTE (TR/TE/$\theta$=20 ms/60 us/10°, 0.7× 0.7×1.4 mm$^3$, 60 sl/3:13 min and STIR-UTE (TI/TR/TE/$\theta$=/120 ms/20 ms/60 us/10°, 0.9×0.9×1.8 mm$^3$, 48 sl/3:29 min. Spine array and 4-channel array was used, as was the gun to puncture tissue.

Methods

Mechanical Deflection: MRT tracking of the path changes in the bovine sample detected changes of 45 and 30 degrees in tip trajectory at penetration depths of 120 and 200 mm, respectively.

Phantom Imaging: (GRE imaging) The 4-channel array provided an SNR enhancement of 8-9× and 7-x, at distances of 6 mm and 8 mm, respectively, from the tube surface, relative to the spine array. Effective FOV is 30×14×14 mm$^3$.

Ex-vivo Imaging: UTE scans displayed strong enhancement at puncture walls. STIR-UTE showed collagen layers within tissue.

The virtual biopsy gun enabled efficient trajectory steering and extremely high CNR imaging within needle punctures, validating the performance of MRI imaging in brachytherapy puncture holes within reasonable scan times. This makes it feasible to use the gun to refine and improve radiation administration.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, devices, systems, computer readable media, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A magnetic resonance imaging (MRI) compatible tissue analysis device, comprising:

at least one sheath comprising at least one channel disposed at least partially therethrough;

at least one elongated probe at least partially disposed and selectively movable within the channel of the sheath, which elongated probe is insertable into at least one tissue, wherein the elongated probe comprises an outer diameter of about 2.2, millimeters or less and wherein one or more grooves each having a substantially flat surface are disposed in the elongated probe, which grooves comprise a depth of about 0.25 millimeters or more;

at least one multilayer radio-frequency (RF) tracking element operably connected to the substantially flat surface of at least one of the grooves of the elongated probe, which RF tracking element is operably connected, or connectable, to at least one MRI apparatus that is configured to track positioning of the elongated probe in substantially real-time at least when the elongated probe is inserted into the tissue and wherein the RF tracking element comprises a thickness of about 0.25 millimeters or less such that the RF tracking element does not extend beyond an outer surface of the elongated probe;

at least one multilayer RF imaging element operably connected to the elongated probe or to the sheath, which RF imaging element is operably connected, or connectable, to the MRI apparatus that is further configured to capture one or more images of the elongated probe and/or the tissue in substantially real-time at least when the elongated probe is inserted into the tissue and wherein the RF imaging element comprises a thickness of about 0.25 millimeters or less;

at least one deflection mechanism operably connected at least to the elongated probe, which deflection mechanism is configured to selectively deflect positioning of at least a portion of the elongated probe; and, at least one handle operably connected at least to the elongated probe and/or to the sheath, wherein the sheath is configured to remain substantially statically straight regardless of a dynamic tension applied by the deflection mechanism, wherein the elongated probe comprises at least one cavity that is disposed substantially through a length of the elongated probe, wherein at least one co-axial cable is at least partially disposed within the cavity and operably connected to the RF tracking element and/or the RF imaging element and operably connected, or connectable, to the MRI apparatus, wherein the deflection mechanism comprises at least one tendon operably connected at least proximal to an end of the elongated probe that is insertable into the tissue and to a tension adjustment element operably connected to the handle, which tendon is at least partially disposed within the cavity and which tension adjustment element is configured to selectively effect deflection of the positioning of the portion of the elongated probe, wherein the elongated probe comprises at least one deflectable region that deflects when the deflection mechanism selectively deflects positioning of the portion of the elongated probe, wherein the deflectable region comprises multiple orifices disposed at least partially through the elongated probe, which orifices communicate with the cavity, wherein at least one of the orifices comprises at least one indentation disposed substantially perpendicular to a longitudinal axis of the elongated probe, and wherein the MRI compatible tissue analysis device produces an effective field of view of at least about 30 mm×14 mm×14 mm when the MRI compatible tissue analysis device is operably connected to the MRI apparatus.

2. The device of claim 1, wherein the RF imaging element is operably connected to the substantially flat surface of at least one of the grooves of the elongated probe.

3. The device of claim 1, wherein the RF tracking element comprises at least one antenna tuned, or tunable, to a magnetic resonance (MR) frequency.

4. The device of claim 1, wherein the deflection mechanism is configured to selectively deflect positioning of at least a tip of the elongated probe.

5. The device of claim 1, comprising at least one collet adapter operably connected to the handle and at least one collect nut adjustably engaged with the collet adapter, which collet adapter and collet nut are configured to adjustably limit radial and/or axial displacement of the elongated probe and/or the sheath relative to the handle.

6. The device of claim 1, comprising at least a portion of at least one axial rotational control mechanism operably connected, or connectable, to the device.

7. A system, comprising at least one magnetic resonance imaging (MRI) compatible tissue analysis device, comprising:

at least one sheath comprising at least one channel disposed at least partially therethrough;

at least one elongated probe at least partially disposed and selectively movable within the channel of the sheath, which elongated probe is insertable into at least one tissue, wherein the elongated probe comprises an outer diameter of about 2.2, millimeters or less and wherein one or more grooves each having a substantially flat surface are disposed in the elongated probe, which grooves comprise a depth of about 0.25 millimeters or more;

at least one multilayer radio-frequency (RF) tracking element operably connected to the substantially flat surface of at least one of the grooves of the elongated probe, wherein the RF tracking element comprises a thickness of about 0.25 millimeters or less such that the RF tracking element does not extend beyond an outer surface of the elongated probe;

at least one multilayer RF imaging element operably connected to the elongated probe or to the sheath, wherein the RF imaging element comprises a thickness of about 0.25 millimeters or less;

at least one deflection mechanism operably connected at least to the elongated probe, which deflection mechanism is configured to selectively deflect positioning of the elongated probe;

at least one handle operably connected at least to the elongated probe and/or to the sheath; and at least one signal amplification mechanism operably connected, or connectable, to the RF tracking element and to the RF imaging element, which signal amplification mechanism is configured to amplify one or more signals received from the RF tracking element and/or from the RF imaging element;

wherein the sheath is configured to remain substantially statically straight regardless of a dynamic tension applied by the deflection mechanism, wherein the elongated probe comprises at least one cavity that is disposed substantially through a length of the elongated probe, wherein at least one co-axial cable is at least partially disposed within the cavity and operably connected to the RF tracking element and/or the RF imaging element and operably connected, or connectable, to the MRI apparatus, wherein the deflection mechanism comprises at least one tendon operably connected at least proximal to an end of the elongated probe that is insertable into the tissue and to a tension adjustment element operably connected to the handle, which tendon is at least partially disposed within the cavity and which tension adjustment element is configured to selectively effect deflection of the positioning of the portion of the elongated probe, wherein the elongated probe comprises at least one deflectable region that deflects when the deflection mechanism selectively deflects positioning of the portion of the elongated probe, wherein the deflectable region comprises multiple orifices disposed at least partially through the elongated probe, which orifices communicate with the cavity, wherein at least one of the orifices comprises at least one indentation disposed substantially perpendicular to a longitudinal axis of the elongated probe; and wherein the MRI compatible tissue analysis device produces an effective field of view of at least about 30 mm×14 mm×14 mm when the MRI compatible tissue analysis device is operably connected to an MRI apparatus; and, at least one MRI apparatus operably connected, or connectable, to the RF tracking element and to the RF imaging element, which MRI apparatus comprises at least one controller that comprises, or is capable of accessing, computer readable media comprising non-transitory computer-executable instructions which, when executed by at least one electronic processor perform at least:

tracking one or more positions of the elongated probe in substantially real-time at least when the elongated probe is inserted into the tissue, and capturing one or more images of the elongated probe and/or the tissue in substantially real-time at least when the elongated probe is inserted into the tissue.

8. The system of claim 7, wherein the signal amplification mechanism is configured to measure the signals before and after being amplified.

9. The system claim 7, wherein the signal amplification mechanism is operably connected to a power source.

10. The system of claim 7, wherein the signal amplification mechanism is operably connected, or connectable, to the RF tracking element and to the RF imaging element via at least one selectively connectable cable that comprises at least one operably connected Balun.

11. The system of claim 7, wherein the signal amplification mechanism is operably connected, or connectable, to the MRI apparatus via at least one cable that comprises at least one operably connected Balun.

12. The system of claim 7, wherein the RF imaging element is operably connected to the substantially flat surface of at least one of the grooves of the elongated probe.

13. The system of claim 7, wherein a system box houses the signal amplification mechanism.

14. A method of analyzing tissue, the method comprising:

positioning a magnetic resonance imaging (MRI) compatible tissue analysis device substantially proximal to at least one tissue, wherein the MRI compatible tissue analysis device produces an effective field of view of at least about 30 mm×14 mm×14 mm when the MRI compatible tissue analysis device is operably connected to at least one MRI apparatus, which tissue analysis device comprises:

at least one sheath comprising at least one channel disposed at least partially therethrough;

at least one elongated probe at least partially disposed and selectively movable within the channel of the sheath, wherein the elongated probe comprises an outer diameter of about 2.2, millimeters or less and wherein one or more grooves each having a substantially flat surface are disposed in the elongated probe, which grooves comprise a depth of about 0.25 millimeters or more;

at least one multilayer RF tracking element operably connected to the substantially flat surface of at least one of the grooves of the elongated probe, wherein the RF tracking element comprises a thickness of about 0.25 millimeters or less such that the RF tracking element does not extend beyond an outer surface of the elongated probe, which RF tracking element is operably connected to the MRI apparatus;

at least one multilayer RF imaging element operably connected to the elongated probe and/or the sheath, wherein the RF imaging element comprises a thickness of about 0.25 millimeters or less, which RF imaging element is operably connected to the MRI apparatus;

at least one deflection mechanism operably connected at least to the elongated probe; and at least one handle operably connected at least to the elongated probe and/or to the sheath;

inserting at least a portion of the elongated probe into the tissue;

wherein the sheath is configured to remain substantially statically straight regardless of a dynamic tension applied by the deflection mechanism, wherein the elongated probe comprises at least one cavity that is disposed substantially through a length of the elongated probe, wherein at least one co-axial cable is at least partially disposed within the cavity and operably connected to the RF tracking element and/or the RF imaging element and operably connected, or connectable, to the MRI apparatus, wherein the deflection mechanism comprises at least one tendon operably connected at least proximal to an end of the elongated probe that is insertable into the tissue and to a tension adjustment element operably connected to the handle, which tendon is at least partially disposed within the cavity and which tension adjustment element is configured to selectively effect deflection of the positioning of the portion of the elongated probe, wherein the elongated probe comprises at least one deflectable region that deflects when the deflection mechanism selectively deflects positioning of the portion of the elongated probe, wherein the deflectable region comprises multiple orifices disposed at least partially through the elongated probe, which orifices communicate with the cavity, and wherein at least one of the orifices comprises at least one indentation disposed substantially perpendicular to a longitudinal axis of the elongated probe; and, tracking one or more positions of the elongated probe in substantially real-time using at least the RF tracking element and the MRI apparatus; and, capturing one or more images of the elongated probe and/or the tissue in substantially real-time using at least the RF imaging element and the MRI apparatus, thereby analyzing the tissue.

15. The method of claim 14, further comprising selectively deflecting at least one position of the elongated probe using the deflection mechanism.

16. The method of claim 14, comprising capturing the images of one or more tissue regions surrounding a hole in the tissue that comprise a diameter of up to about 100 mm around the hole, when the elongated probe is inserted in the hole in the tissue.

17. The method of claim 14, comprising capturing the images of the tissue along a length of a hole in the tissue that extends up to about 100 mm, when the elongation probe is inserted in the hole.

18. The method of claim 14, comprising analyzing the tissue in-situ in a subject.

19. The method of claim 14, wherein the device comprises at least a portion of at least one axial rotational control mechanism operably connected to the elongated probe and wherein the method further comprises indicating at least one rotational angle formed between at least a portion of the elongated probe and at least one template device that is positioned at least proximal to the tissue.

* * * * *